(12) United States Patent
Zhou

(10) Patent No.: US 7,919,098 B2
(45) Date of Patent: Apr. 5, 2011

(54) ERBB-3 BASED METHODS AND COMPOSITIONS FOR TREATING NEOPLASMS

(75) Inventor: Mingdong Zhou, Shanghai (CN)

(73) Assignee: Zensun ( Shanghai ) Sci & Tech Co., Ltd., Shanghai (CN)

( * ) Notice: Subject to any disclaimer, the term of this patent is extended or adjusted under 35 U.S.C. 154(b) by 853 days.

(21) Appl. No.: 10/516,759

(22) PCT Filed: Mar. 26, 2003

(86) PCT No.: PCT/CN03/00217

§ 371 (c)(1),
(2), (4) Date: Mar. 3, 2006

(87) PCT Pub. No.: WO03/080835

PCT Pub. Date: Oct. 2, 2003

(65) Prior Publication Data

US 2008/0057064 A1  Mar. 6, 2008

(30) Foreign Application Priority Data

Mar. 26, 2002 (CN) .................................. 02 1 16259

(51) Int. Cl.
  A61K 39/00 (2006.01)
  A61K 38/00 (2006.01)
(52) U.S. Cl. ............................ 424/185.1; 514/2; 514/44
(58) Field of Classification Search .......................... None
  See application file for complete search history.

(56) References Cited

U.S. PATENT DOCUMENTS

| | | | |
|---|---|---|---|
| 5,183,884 A * | 2/1993 | Kraus et al. .................. | 536/23.5 |
| 5,480,968 A | 1/1996 | Kraus et al. | |
| 5,578,482 A | 11/1996 | Lippman et al. | |
| 5,686,102 A | 11/1997 | Gross et al. | |
| 5,736,154 A | 4/1998 | Fuisz | |
| 5,741,511 A | 4/1998 | Lee et al. | |
| 5,820,859 A | 10/1998 | Kraus et al. | |
| 5,886,039 A | 3/1999 | Kock et al. | |
| 5,941,868 A | 8/1999 | Kaplan et al. | |
| 5,968,511 A | 10/1999 | Akita et al. | |
| 6,197,801 B1 | 3/2001 | Lin | |
| 6,258,374 B1 | 7/2001 | Friess et al. | |
| 7,285,649 B2 | 10/2007 | Akita et al. | |
| 2004/0197332 A1 | 10/2004 | Ullrich et al. | |
| 2005/0136494 A1 | 6/2005 | Akita et al. | |

FOREIGN PATENT DOCUMENTS

| | | |
|---|---|---|
| EP | 0 896 586 | 6/1991 |
| EP | 0 502 927 | 10/1997 |
| WO | WO 91/02062 | 2/1991 |
| WO | WO 91/08214 | 6/1991 |
| WO | WO 97/35885 | 10/1997 |
| WO | WO 98/02540 * | 1/1998 |
| WO | WO 98/17797 A1 | 4/1998 |
| WO | WO 98/30704 | 7/1998 |
| WO | WO 98/35036 | 8/1998 |
| WO | WO 01/87334 | 11/2001 |
| WO | WO 03/013602 | 2/2003 |
| WO | WO 2006/091209 | 8/2006 |
| WO | WO 2008/100624 | 8/2008 |

OTHER PUBLICATIONS

Plowman et al (PNAS, 1990, 87:4905-4909).*
Kraus et al (PNAS, 1989, 86:9193-9197).*
Lee et al (Cancer Research, 2001, 61:4467-4473).*
Lee et al (Cancer Research, 2001, 61:4467-4473).*
Kraus et al (PNAS 1989, 9193-9197).*
Alimandi et al., 1995, "Cooperative signaling of ErbB3 and ErbB2 in neoplastic transformation and human mammary carcinomas." Oncogene 10:1813-1821.
Auerbach & Auerbach, 1994, "Angiogenesis inhibition: A review." Pharmacol. Ther. 63(3):265-311.
Bei et al., 1999, "Immune Responses to all ErbB family receptors detectable in serum of cancer patients." Oncogene 18(6):1267-1275.
Chan et al., 1995, "Heregulin activation of extracellular acidification in mammary carcinoma cells is associated with expression of HER2 and HER3." J. Biol. Chem. 270:22608-22613.
Chen et al., 1996, "An Immunological Approach Reveals Biological Differences between the Two NDF/Heregulin Receptors, ErbB-3 and ErbB-4" J Biol. Chem. 271:7620-7629.
Cooper, 2000, *The Cell; A molecular approach*, "Section 13: Cell Signaling; Receptor Protein-Tyrosine Kinase," $2^{nd}$ edition. ASM Press, Washington DC, pp. 1-6, Accessed Sep. 15, 2005 from http://www.ncbi.nlm.nih.gov/books/bv.fcgi?rid=cooper.
Curti, 1993, "Physical barriers to drug delivery in tumors" Crit. Rev. in Oncology/Hematology 14:29-39.
Dermer, 1994, "Another Anniversary for the War on Cancer." Bio/technology 12:320.
Drebin et al., 1988, "Monoclonal antibodies reactive with distinct domains of the *neu* oncogene-encoded p185 molecule exert synergistic anti-tumor effects in vivo." Oncogene 2:273-277.

(Continued)

*Primary Examiner* — Laura B Goddard
(74) *Attorney, Agent, or Firm* — Jones Day

(57) ABSTRACT

The present invention relates to compositions and methods for treating neoplasms in mammals, particularly humans. More particularly, the present invention provides for methods for preventing, treating or delaying neoplasm in a mammal using an ErbB-3 protein, a nucleic acid encoding an ErbB-3 protein or a functional fragment thereof. The present invention also provides for isolated nucleic acids encoding an extracellular domain of the ErbB-3 protein, or a functional fragment thereof, substantially purified extracellular domain of the ErbB-3 protein, or a functional fragment thereof and antibodies that bind to an epitope in an extracellular domain of the ErbB-3 protein, or a functional fragment thereof. The present invention further provides for pharmaceutical compositions and/or vaccines comprising the extracellular domain of the ErbB-3 protein, or a functional fragment thereof, or nucleic acids encoding and antibodies binding to such extracellular domain or functional fragments thereof.

13 Claims, 12 Drawing Sheets

OTHER PUBLICATIONS

Fendly et al., 1990, "Characterization of Murine Monoclonal Antibodies Reactive to Either the Human Epidermal Growth Factor Receptor or HER2/neu Gene Product." Cancer Res. 50:1550-1558.

Freshney, 1983, Culture of Animal cells: A manual of Basic Technique. Alan R. Liss., Inc. New York.

Gellner & Brenner, 1999, "Analysis of 148 kb of genomic DNA around the wnt1 locus of Fugu rubripes." Genome Res 9(3):251-258.

Genbank Accesion No. AF056116, "Fugu rubripes serine/threonine kinase receptor type1, All-1 related protein (ALR), fugu hedgehog (fhh), Ikaros-like, wnt1, wnt10b, ARF3, erbB3, PAS1, and L41 ribosomal protein genes, complete cds; LRP1 gene, partial cds; and unknown genes," dated Apr. 15, 1999.

Genbank Accesion No. M29366, "Human epidermal growth factor receptor (ERBB3) mRNA, complete cds," dated Apr. 23, 1993.

Genbank Accession No. U29339, "Rattus norvegicus ErbB3/Her3 precursor mRNA, complete cds," dated Dec. 5, 2001.

Gura, 1997, "Systems for identifying new drugs are often faulty." Science 278:1041-1042.

Hamid, 2004, "Emerging Treatments in Oncology: Focus on Tyrosine Kinase (erbB) Receptor Inhibitors." J Am. Pharm Assoc. 44:52-58.

Hellyer et al., 1995, "Cloning of the rat ErbB3 cDNA and characterization of the recombinant protein." Gene 165(2):279-284.

Holbro et al., 2003, "The ErbB2/ErbB3 heterodimer functions as an oncogenic unit: ErbB2 requires ErbB3 to drive breast tumor cell proliferation." Proc. Natl. Acad. Sci. 100:8933-8938.

Hudson & Souriau, 2003, "Engineered antibodies." Nat. Med. 9:129-134.

International Search Report of Application No. PCT/AU00/00671, dated Aug. 30, 2000.

International Search Report of Application No. PCT/CN03/00217, dated Jun. 5, 2003.

Jain, 1994, "Barriers to drug delivery in solid tumors." Sci. Am. 271:58-65.

Kasprzyk et al., 1992, "Therapy of an Animal Model of Human Gastric Cancer Using a Combination of Anti-erbB-2 Monoclonal Antibodies." Cancer Res. 52:2771-2776.

Klapper et al., 1997, "A Subclass of Tumor-Inhibitory Monoclonal Antibodies to Erb-2/HER2 Blocks Crosstalk with Growth Factor Receptors." Oncogene 14:2099-2109.

Klapper et al., 1999, "The ErB-2/HER2 Oncoprotein of Human Carcinomas May Function soley as a shared coreceptor for multiple Stroma-Derived Growth Factors." Proc. Natl. Acad. Sci 96:4995-5000.

Kraus et al., 1989, "Isolation and characterization of ERBB3, a third member of the ERBB/epidermal growth factor receptor family: evidence for overexpression in a subset of human mammary tumors." Proc. Natl. Acad. Sci. 86:9193-9197.

Lab Vision NeoMarkers data sheet (Ab105) "c-erbB-3/HER-3 Ab-5 (Clone H3.105.5; same as Ab105)" Accessed Feb. 23, 2008 from http://www.labvision.com.

Lee et al., 2001, "A naturally occurring secreted human ErbB3 receptor isoform inhibits heregulin-stimulated activation of ErbB2, ErbB3, and ErbB4." Cancer Res 61:4467-4473.

Lillehoj et al., 1993, "Adjuvanticity of dimethyl dioctadecyl ammonium bromide, complete Freund's adjuvant and Corynebacterium parvum with respect to host immune response to coccidial antigens." Avian Dis 37(3):731-740.

Mendrola et al., 2002, "The Single Transmembrane Domains of ErbB Receptors Self-associate in Cell Membranes." J. Biol. Chem. 27:4704-4712.

Park et al., 1999, "Induction of the Tat-Binding Protein 1 Gene Accompanies the Disabling of Oncogenic ErbB receptor tyrosine kinaes." Proc. Natl. Acad. Sci 96:6434-6438.

Pinkas-Kramarski et al., 1998, "The Oncogenic ErbB-2/ErbB-3 Heterodimer is a Surrogate Receptor fo Epidermal Growth Factor and Betacellulin." Oncogene 16:1249-1258.

Plowman et al., 1990, "Molecular cloning and expression of an additional epidermal growth factor receptor-related gene." Proc. Natl. Acad. Sci 87:4905-4909.

Ram et al., 1996, "Mitogenic Activity of Neu Differentiation Factor// Heregulin Mimics that of Epidermal Growth Factor and Insulin-Like Growth Factor-I in Human Mammary epithelial cells." J. cell. Physiol 169:589-596.

Ratiff et al, 1992, "Role of the immune response in BCG for bladder cancer." Eur. Urol. 2 (Suppl):17-21.

Schaefer et al., 2006, "Potential use of humanized antibodies in the treatment of breast cancer." Expert Rev. Anticancer. Ther. 6:1065-1074.

Sliwkowski et al., 1995, "Co-Expression of erbB2 and erbB3 Proteins Reconstitutes a High Affinity Receptro for Heregulin." J. Biolog. Chem. 269(20):14661-14665.

Stancovski et al., 1991, "Mechanistic aspects of the opposing effects of monoclonal antibodies to the ERBB2 receptor on tumor growth." Proc. Natl. Acad. Sci. 88:8691-8695.

Stern & Herrman, 2005, "Overview of monoclonal antibodies in cancer therapy: present and promise." Crit. Rev in Oncology/Hematology 54:11-29.

Supplementary European Search Report for European Application No. EP 00 93 6539, mailed on Apr. 29, 2005.

Vijapurkar et al., 1998, "Mutation of a Shc Binding Site tyrosine residue in ErbB3/Her3 Blocks Heregulin Dependent Activaton of Mitogen-Activated Protein Kinase." J. Biol. Chem. 273(33):20996-21002.

Yeon & Pegram, 2005, "Anti-erbB-2 antibody trastuzumab in the treatment of HER2-amplified breast cancer." Invest. New Drugs 23:391-409.

Gyorffy et al., "Adenoviral vector expressing murine angiostatin inhibits a model of breast cancer metastatic growth in the lungs of mice," Am J Pathol 2001, 159:1137-1147.

Bandyopadhyay et al., "Physical interaction between epidermal growth factor receptor and DNA-dependent protein kinase in mammalian cells," J Biol Chem., 1998, 273: 1568-1573.

Faress et al, "Bleomycin-induced pulmonary fibrosis is attenuated by a monoclonal antibody targeting HER2," J Appl Physiol., 2007 103: 2077-2083.

Hudziak et al., "p185HER2 monoclonal antibody has antiproliferative effects in vitro and sensitizes human breast tumor cells to tumor necrosis factor," 1989, Mol Cell Biol, 9: 1165-1172.

International Preliminary Examination Report of PCT/AU00/00671.

Levy et al., "Biological and clinical implications of lymphocyte hybridomas: tumor therapy with monoclonal antibodies," Annu Rev Med , 1983, 34: 107-116.

Lewis et al., "Differential responses of human tumor cell lines to anti-p185HER2 monoclonal antibodies," Cancer Immunol Immunothet., 1993, 37: 255-263.

Lewis et al., "Growth regulation of human breast and ovarian tumor cells by heregulin: Evidence for the requirement of ErbB2 as a critical component in mediating heregulin responsiveness," Cancer Res , 1996, 56: 1457-1465.

Schroff et al, "T65 antigen modulation in a phase I monoclonal antibody trial with chronic lymphocytic leukemia patients," J Immunol., 1984, 133: 1641-1648.

Stoica et al,, "Effect of estradiol on estrogen receptor-alpha gene expression and activity can be modulated by the ErbB2/PI 3-K/Akt pathway," Oncogene, 2003, 22: 7998-8011.

Vadlamudi et al., "Regulation of cyclooxygenase-2 pathway by HER2 receptor," Oncogene, 1999, 18: 305-314.

Wang et al., "Reciprocal interactions between beta1-integrin and epidermal growth factor receptor in three-dimensional basement membrane breast cultures: a different perspective in epithelial biology," Proc Natl Acad Sci U S A., 1998, 95: 14821-14826.

Xu et al., "Antibody-induced growth inhibition is mediated through immunochemically and functionally distinct epitopes on the extracellular domain of the c-erbB-2 (HER-2/neu) gene product p185," Int J Cancer, 1993, 53: 401-408.

Ye et al., "Augmentation of a humanized anti-HER2 mAb 4D5 induced growth inhibition by a human-mouse chimeric anti-EGF receptor mAb C225," Oncogene, 1999, 18: 731-738.

\* cited by examiner

```
agggcgaa cgacgctctg caggtgctgg gcttgctttt cagcctggcc cggggctccg
aggtgggcaa ctctcaggca gtgtgtcctg ggactctgaa tggcctgagt gtgaccggcg
atgctgagaa ccaataccag acactgtaca agctctacga gaggtgtgag gtggtgatgg
ggaaccttga gattgtgctc acgggacaca atgccgacct ctccttcctg cagtggattc
gagaagtgac aggctatgtc ctcgtggcca tgaatgaatt ctctactcta ccattgccca
acctccgcgt ggtgcgaggg acccaggtct acgatgggaa gtttgccatc ttcgtcatgt
tgaactataa caccaactcc agccacgctc tgcgccagct ccgcttgact cagctcaccg
agattctgtc aggggggtgtt tatattgaga agaacgataa gctttgtcac atggacacaa
ttgactggag ggacatcgtg agggaccgag atgctgagat agtggtgaag gacaatggca
gaagctgtcc cccctgtcat gaggtttgca agggggcgatg ctggggtcct ggatcagaag
actgccagac attgaccaag accatctgtg ctcctcagtg taatggtcac tgctttgggc
ccaaccccaa ccagtgctgc catgatgagt gtgccggggg ctgctcaggc cctcaggaca
cagactgctt tgcctgccgg cacttcaatg acagtggagc ctgtgtacct cgctgtccac
agcctcttgt ctacaacaag ctaactttcc agctggaacc caatccccac accaagtatc
agtatggagg agtttgtgta gccagctgtc cccataactt tgtggtggat caaacatcct
gtgtcagggc ctgtcctcct gacaagatgg aagtagataa aaatgggctc aagatgtgtg
agccttgtgg gggactatgt cccaaagcct gtgagggaac aggctctggg agccgcttcc
agactgtgga ctcgagcaac attgatggat ttgtgaactg caccaagatc ctgggcaacc
tggactttct gatcaccggc ctcaatggag acccctggca caagatccct gccctggacc
cagagaagct caatgtcttc cggacagtac gggagatcac aggttacctg aacatccagt
cctggccgcc ccacatgcac aacttcagtg ttttttccaa tttgacaacc attggaggca
gaagcctcta caaccggggc ttctcattgt tgatcatgaa gaacttgaat gtcacatctc
tgggcttccg atccctgaag gaaattagtg ctgggcgtat ctatataagt gccaataggc
agctctgcta ccaccactct ttgaactgga ccaaggtgct tcgggggcct acggaagagc
gactagacat caagcataat cggccgcgca gagactgcgt ggcagagggc aaagtgtgtg
acccactgtg ctcctctggg ggatgctggg gcccaggccc tggtcagtgc ttgtcctgtc
gaaattatag ccgaggaggt gtctgtgtga cccactgcaa ctttctgaat ggggagcctc
gagaatttgc ccatgaggcc gaatgcttct cctgccaccc ggaatgccaa cccatggagg
gcactgccac atgcaatggc tcgggctctg atacttgtgc tcaatgtgcc catttttcgag
atgggcccca ctgtgtgagc agctgccccc atggagtcct aggtgccaag ggcccaatct
acaagtaccc agatgttcag aatgaatgtc ggccctgcca tgagaactgc acccagggggt gtaaaggacc agagcttcaa gactgtttag gacaaacact ggtgctgatc ggcaaa FLAG
```

Fig. 1 (SEQ ID NO: 4)

TTTCTGCGGAGTCATG
(SEQ ID NO: 8)

```
  1 MRANDALQVL GLLFSLARGS EVGNSQAVCP GTLNGLSVTG DAENQYQTLY KLYERCEVVM
 61 GNLEIVLTGH NADLSFLQWI REVTGYVLVA MNEFSTLPLP NLRVVRGTQV YDGKFAIFVM
121 LNYNTNSSHA LRQLRLTQLT EILSGGVYIE KNDKLCHMDT IDWRDIVRDR DAEIVVKDNG
181 RSCPPCHEVC KGRCWGPGSE DCQTLTKTIC APQCNGHCFG PNPNQCCHDE CAGGCSGPQD
241 TDCFACRHFN DSGACVPRCP QPLVYNKLTF QLEPNPHTKY QYGGVCVASC PHNFVVDQTS
301 CVRACPPDKM EVDKNGLKMC EPCGGLCPKA CEGTGSGSRF QTVDSSNIDG FVNCTKILGN
361 LDFLITGLNG DPWHKIPALD PEKLNVFRTV REITGYLNIQ SWPPHMHNFS VFSNLTTIGG
421 RSLYNRGFSL LIMKNLNVTS LGFRSLKEIS AGRIYISANR QLCYHHSLNW TKVLRGPTEE
481 RLDIKHNRPR RDCVAEGKVC DPLCSSGGCW GPGPGQCLSC RNYSRGGVCV THCNFLNGEP
541 REFAHEAECF SCHPECQPME GTATCNGSGS DTCAQCAHFR DGPHCVSSCP HGVLGAKGPI
601 YKYPDVQNEC RPCHENCTQG CKGPELQDCL GQTLVLIGKT
```

Fig. 5 (SEQ ID NO: 2)

```
gatcctgtcctg ggactctgaa tggcctgagt gtgaccggcg atgctgagaa ccaataccag
   acactgtaca agctctacga gaggtgtgag gtggtgatgg ggaaccttga gattgtgctc
   acgggacaca atgccgacct ctccttcctg cagtggattc gagaagtgac aggctatgtc
   ctcgtggcca tgaatgaatt ctctactcta ccattgccca acctccgcgt ggtgcgaggg
   acccaggtct acgatgggaa gtttgccatc ttcgtcatgt gaactataa caccaactcc
   agccacgctc tgcgccagct ccgcttgact cagctcaccg agattctgtc agggggtgtt
   tatattgaga agaacgataa gctttgtcac atggacacaa ttgactggag ggacatcgtg
   agggaccgag atgctgagat agtggtgaag gacaatggca gaagcTGA ctcga
```

Fig. 6 (SEQ ID NO: 5)

1  2  3  4

1  2  3  4  5  6  7  8

```
  1  MRANDALQVL GLLFSLARGS EVGNSQAVCP GTLNGLSVTG DAENQYQTLY KLYERCEVVM
 61  GNLEIVLTGH NADLSFLQWI REVTGYVLVA MNEFSTLPLP NLRVVRGTQV YDGKFAIFVM
121  LNYNTNSSHA LRQLRLTQLT EILSGGVYIE KNDKLCHMDT IDWRDIVRDR DAEIVVKDNG
181  RSCPPCHEVC
```

Fig11 (SEQ ID NO: 3)

Anti-tumor Efficacy of The Neu-targeted Vaccine

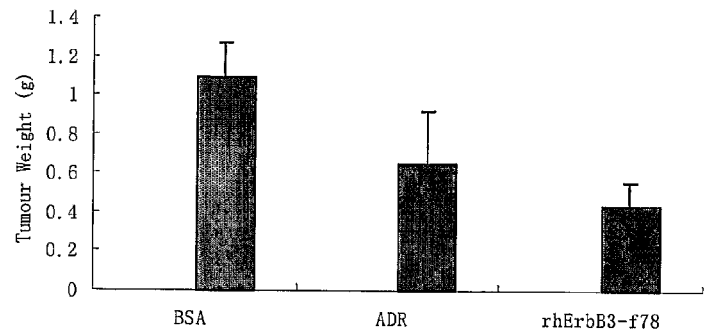

Fig.22

```
  1 atgaaatacctgctgccgaccgctgctgctggtctgctgctcctc
    _M  K  Y  L  L  P  T  A  A  A  G  L  L  L  L
 46 gctgcccagccggcgatggccatggacatcaagcataatcggccg
     A  A  Q  P  A  M  A  M  D  I  K  H  N  R  P
 91 cgcagagactgcgtggcagagggcaaagtgtgtgacccactgtgc
     R  R  D  C  V  A  E  G  K  V  C  D  P  L  C
136 tcctctgggggatgctggggcccaggccctggtcagtgcttgtcc
     S  S  G  G  C  W  G  P  G  P  G  Q  C  L  S
181 tgtcgaaattatagccgaggaggtgtctgtgtgacccactgcaac
     C  R  N  Y  S  R  G  G  V  C  V  T  H  C  N
226 tttctgaatggggagcccctcgagcaccaccaccaccaccactga  (SEQ ID NO:17)
     F  L  N  G  E  P  L  E  H  H  H  H  H         (SEQ ID NO:14)
```

Fig. 23

ATGGTTTGTGTAGCCAGCTGTCCCCATAACTTTGTGGTGGATCAAACATCCTGTGTCA
GGGCCTGTCCTCCTGACAAGATGGAAGTAGATAAAAATGGGCTCAAGATGTGTGAGC
CTTGTGGGGACTATGTCCCAAAGCCTGTGAGGGAACAGGCTCTGGGAGCCGCTTCCA
GACTGTGGACTCGAGCAACATTGATGGATTTGTGAACTGCACCAAGATCCTGGGCAAC
CTGGACTTTCTGATCACCGGCCTCAATGGAGACCCCTGGCACAAGATCCCTGCCCTGG
ACCCAGAGAAGCTCAATGTCTTCCGGACAGTACGGGAGATCACAGGTTACCTGAACA
TCCAGTCCTGGCCGCCCCACATGCACAACTTCAGTGTTTTTTCCAATTTGACAACCATT
GGAGGCAGAAAGCTTGCGGCCGCACTCGAGCACCACCACCACCACCACTGA

Fig.24(SEQ ID NO :15)

Met V C V A S C P H N F V V D Q T S C V R A C P P D K Met E V D K N G L K Met C E P C
G G L C P K A C E G T G S G S R F Q T V D S S N I D G F V N C T K I L G N L D F L I T G L
N G D P W H K I P A L D P E K L N V F R T V R E I T G Y L N I Q S W P P H Met H N F S V
F S N L T T I G G R S K L A A A L E H H H H H

Fig.25(SEQ ID NO :16)

SEQUENCE LISTING

<160> NUMBER OF SEQ ID NOS: 17

<210> SEQ ID NO 1
<211> LENGTH: 1342
<212> TYPE: PRT
<213> ORGANISM: Homo sapiens

<400> SEQUENCE: 1

```
Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365
```

```
Asn Gly Asp Pro Trp His Lys Ile Pro Ala Leu Asp Pro Glu Lys Leu
    370                 375             380

Asn Val Phe Arg Thr Val Arg Glu Ile Thr Gly Tyr Leu Asn Ile Gln
385                 390             395                 400

Ser Trp Pro Pro His Met His Asn Phe Ser Val Phe Ser Asn Leu Thr
                405             410              415

Thr Ile Gly Gly Arg Ser Leu Tyr Asn Arg Gly Phe Ser Leu Leu Ile
            420             425             430

Met Lys Asn Leu Asn Val Thr Ser Leu Gly Phe Arg Ser Leu Lys Glu
    435             440             445

Ile Ser Ala Gly Arg Ile Tyr Ile Ser Ala Asn Arg Gln Leu Cys Tyr
    450             455             460

His His Ser Leu Asn Trp Thr Lys Val Leu Arg Gly Pro Thr Glu Glu
465             470             475                 480

Arg Leu Asp Ile Lys His Asn Arg Pro Arg Arg Asp Cys Val Ala Glu
            485             490             495

Gly Lys Val Cys Asp Pro Leu Cys Ser Ser Gly Gly Cys Trp Gly Pro
            500             505             510

Gly Pro Gly Gln Cys Leu Ser Cys Arg Asn Tyr Ser Arg Gly Gly Val
        515             520             525

Cys Val Thr His Cys Asn Phe Leu Asn Gly Glu Pro Arg Glu Phe Ala
        530             535             540

His Glu Ala Glu Cys Phe Ser Cys His Pro Glu Cys Gln Pro Met Glu
545             550             555                 560

Gly Thr Ala Thr Cys Asn Gly Ser Gly Ser Asp Thr Cys Ala Gln Cys
                565             570             575

Ala His Phe Arg Asp Gly Pro His Cys Val Ser Ser Cys Pro His Gly
            580             585             590

Val Leu Gly Ala Lys Gly Pro Ile Tyr Lys Tyr Pro Asp Val Gln Asn
        595             600             605

Glu Cys Arg Pro Cys His Glu Asn Cys Thr Gln Gly Cys Lys Gly Pro
    610             615             620

Glu Leu Gln Asp Cys Leu Gly Gln Thr Leu Val Leu Ile Gly Lys Thr
625             630             635                 640

His Leu Thr Met Ala Leu Thr Val Ile Ala Gly Leu Val Val Ile Phe
                645             650             655

Met Met Leu Gly Gly Thr Phe Leu Tyr Trp Arg Gly Arg Arg Ile Gln
            660             665             670

Asn Lys Arg Ala Met Arg Arg Tyr Leu Glu Arg Gly Glu Ser Ile Glu
    675             680             685

Pro Leu Asp Pro Ser Glu Lys Ala Asn Lys Val Leu Ala Arg Ile Phe
    690             695             700

Lys Glu Thr Glu Leu Arg Lys Leu Lys Val Leu Gly Ser Gly Val Phe
705             710             715                 720

Gly Thr Val His Lys Gly Val Trp Ile Pro Glu Gly Glu Ser Ile Lys
            725             730             735

Ile Pro Val Cys Ile Lys Val Ile Glu Asp Lys Ser Gly Arg Gln Ser
            740             745             750

Phe Gln Ala Val Thr Asp His Met Leu Ala Ile Gly Ser Leu Asp His
        755             760             765

Ala His Ile Val Arg Leu Leu Gly Leu Cys Pro Gly Ser Ser Leu Gln
    770             775             780

Leu Val Thr Gln Tyr Leu Pro Leu Gly Ser Leu Leu Asp His Val Arg
```

-continued

```
            785                 790                 795                 800
Gln His Arg Gly Ala Leu Gly Pro Gln Leu Leu Asn Trp Gly Val
                    805                 810                 815
Gln Ile Ala Lys Gly Met Tyr Tyr Leu Glu Glu His Gly Met Val His
                    820                 825                 830
Arg Asn Leu Ala Ala Arg Asn Val Leu Leu Lys Ser Pro Ser Gln Val
                    835                 840                 845
Gln Val Ala Asp Phe Gly Val Ala Asp Leu Leu Pro Pro Asp Asp Lys
                    850                 855                 860
Gln Leu Leu Tyr Ser Glu Ala Lys Thr Pro Ile Lys Trp Met Ala Leu
865                 870                 875                 880
Glu Ser Ile His Phe Gly Lys Tyr Thr His Gln Ser Asp Val Trp Ser
                    885                 890                 895
Tyr Gly Val Thr Val Trp Glu Leu Met Thr Phe Gly Ala Glu Pro Tyr
                    900                 905                 910
Ala Gly Leu Arg Leu Ala Glu Val Pro Asp Leu Leu Glu Lys Gly Glu
                    915                 920                 925
Arg Leu Ala Gln Pro Gln Ile Cys Thr Ile Asp Val Tyr Met Val Met
        930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Pro Arg Tyr Leu
                    965                 970                 975
Val Ile Lys Arg Glu Ser Gly Pro Gly Ile Ala Pro Gly Pro Glu Pro
                    980                 985                 990
His Gly Leu Thr Asn Lys Lys Leu Glu Glu Val Glu Leu Glu Pro Glu
                    995                 1000                1005
Leu Asp Leu Asp Leu Asp Leu Glu Ala Glu Glu Asp Asn Leu Ala Thr
        1010                1015                1020
Thr Thr Leu Gly Ser Ala Leu Ser Leu Pro Val Gly Thr Leu Asn Arg
1025                1030                1035                1040
Pro Arg Gly Ser Gln Ser Leu Leu Ser Pro Ser Ser Gly Tyr Met Pro
                    1045                1050                1055
Met Asn Gln Gly Asn Leu Gly Glu Ser Cys Gln Glu Ser Ala Val Ser
                    1060                1065                1070
Gly Ser Ser Glu Arg Cys Pro Arg Pro Val Ser Leu His Pro Met Pro
            1075                1080                1085
Arg Gly Cys Leu Ala Ser Glu Ser Ser Glu Gly His Val Thr Gly Ser
            1090                1095                1100
Glu Ala Glu Leu Gln Glu Lys Val Ser Met Cys Arg Ser Arg Ser Arg
1105                1110                1115                1120
Ser Arg Ser Pro Arg Pro Arg Gly Asp Ser Ala Tyr His Ser Gln Arg
                    1125                1130                1135
His Ser Leu Leu Thr Pro Val Thr Pro Leu Ser Pro Pro Gly Leu Glu
                    1140                1145                1150
Glu Glu Asp Val Asn Gly Tyr Val Met Pro Asp Thr His Leu Lys Gly
                    1155                1160                1165
Thr Pro Ser Ser Arg Glu Gly Thr Leu Ser Ser Val Gly Leu Ser Ser
                    1170                1175                1180
Val Leu Gly Thr Glu Glu Glu Asp Glu Asp Glu Glu Tyr Glu Tyr Met
1185                1190                1195                1200
Asn Arg Arg Arg Arg His Ser Pro Pro His Pro Pro Arg Pro Ser Ser
                    1205                1210                1215
```

```
Leu Glu Glu Leu Gly Tyr Glu Tyr Met Asp Val Gly Ser Asp Leu Ser
               1220                1225                1230

Ala Ser Leu Gly Ser Thr Gln Ser Cys Pro Leu His Pro Val Pro Ile
        1235                1240                1245

Met Pro Thr Ala Gly Thr Thr Pro Asp Glu Asp Tyr Glu Tyr Met Asn
    1250                1255                1260

Arg Gln Arg Asp Gly Gly Pro Gly Gly Asp Tyr Ala Ala Met Gly
1265            1270            1275                    1280

Ala Cys Pro Ala Ser Glu Gln Gly Tyr Glu Glu Met Arg Ala Phe Gln
                1285            1290                1295

Gly Pro Gly His Gln Ala Pro His Val His Tyr Ala Arg Leu Lys Thr
            1300            1305                1310

Leu Arg Ser Leu Glu Ala Thr Asp Ser Ala Phe Asp Asn Pro Asp Tyr
        1315            1320                1325

Trp His Ser Arg Leu Phe Pro Lys Ala Asn Ala Gly Arg Thr
        1330            1335                1340

<210> SEQ ID NO 2
<211> LENGTH: 640
<212> TYPE: PRT
<213> ORGANISM: Homo sapiens

<400> SEQUENCE: 2

Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255
```

```
Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
        370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
    530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
        610                 615                 620

Glu Leu Gln Asp Cys Leu Gly Gln Thr Leu Val Leu Ile Gly Lys Thr
625                 630                 635                 640

<210> SEQ ID NO 3
<211> LENGTH: 190
<212> TYPE: PRT
<213> ORGANISM: Homo sapiens

<400> SEQUENCE: 3
```

```
Met Arg Ala Asn Asp Ala Leu Gln Val Leu Gly Leu Leu Phe Ser Leu
1               5                   10                  15
Ala Arg Gly Ser Glu Val Gly Asn Ser Gln Ala Val Cys Pro Gly Thr
            20                  25                  30
Leu Asn Gly Leu Ser Val Thr Gly Asp Ala Glu Asn Gln Tyr Gln Thr
        35                  40                  45
Leu Tyr Lys Leu Tyr Glu Arg Cys Glu Val Val Met Gly Asn Leu Glu
    50                  55                  60
Ile Val Leu Thr Gly His Asn Ala Asp Leu Ser Phe Leu Gln Trp Ile
65                  70                  75                  80
Arg Glu Val Thr Gly Tyr Val Leu Val Ala Met Asn Glu Phe Ser Thr
                85                  90                  95
Leu Pro Leu Pro Asn Leu Arg Val Val Arg Gly Thr Gln Val Tyr Asp
            100                 105                 110
Gly Lys Phe Ala Ile Phe Val Met Leu Asn Tyr Asn Thr Asn Ser Ser
        115                 120                 125
His Ala Leu Arg Gln Leu Arg Leu Thr Gln Leu Thr Glu Ile Leu Ser
    130                 135                 140
Gly Gly Val Tyr Ile Glu Lys Asn Asp Lys Leu Cys His Met Asp Thr
145                 150                 155                 160
Ile Asp Trp Arg Asp Ile Val Arg Asp Arg Asp Ala Glu Ile Val Val
                165                 170                 175
Lys Asp Asn Gly Arg Ser Cys Pro Pro Cys His Glu Val Cys
            180                 185                 190

<210> SEQ ID NO 4
<211> LENGTH: 1914
<212> TYPE: DNA
<213> ORGANISM: Homo sapiens

<400> SEQUENCE: 4
agggcgaacg acgctctgca ggtgctgggc ttgcttttca gcctggcccg gggctccgag      60
gtgggcaact ctcaggcagt gtgtcctggg actctgaatg gcctgagtgt gaccggcgat     120
gctgagaacc aataccagac actgtacaag ctctacgaga ggtgtgaggt ggtgatgggg     180
aaccttgaga ttgtgctcac gggacacaat gccgacctct ccttcctgca gtggattcga     240
gaagtgacag gctatgtcct cgtggccatg aatgaattct ctactctacc attgcccaac     300
ctccgcgtgg tgcgagggac ccaggtctac gatgggaagt ttgccatctt cgtcatgttg     360
aactataaca ccaactccag ccacgctctg cgccagctcc gcttgactca gctcaccgag     420
attctgtcag ggggtgttta tattgagaag aacgataagc tttgtcacat ggacacaatt     480
gactggaggg acatcgtgag ggaccgagat gctgagatag tggtgaagga caatggcaga     540
agctgtcccc cctgtcatga ggtttgcaag gggcgatgct ggggtcctgg atcagaagac     600
tgccagacat tgaccaagac catctgtgct cctcagtgta atggtcactg ctttgggccc     660
aaccccaacc agtgctgcca tgatgagtgt gccggggct gctcaggccc tcaggacaca     720
gactgctttg cctgccggca cttcaatgac agtggagcct gtgtacctcg ctgtccacag     780
cctcttgtct acaacaagct aactttccag ctggaaccca tccccacac caagtatcag     840 tatggaggag tttgtgtagc cagctgtccc cataactttg tggtggatca acatcctgt     900 gtcagggcct gtcctcctga caagatggaa gtagataaaa atgggctcaa gatgtgtgag     960
ccttgtgggg gactatgtcc caaagcctgt gagggaacag ctctgggag ccgcttccag    1020 actgtggact cgagcaacat tgatggattt gtgaactgca ccaagatcct gggcaacctg    1080
```

```
gactttctga tcaccggcct caatggagac ccctggcaca agatccctgc cctggaccca      1140
gagaagctca atgtcttccg gacagtacgg gagatcacag gttacctgaa catccagtcc      1200
tggccgcccc acatgcacaa cttcagtgtt ttttccaatt tgacaaccat tggaggcaga      1260
agcctctaca accggggctt ctcattgttg atcatgaaga acttgaatgt cacatctctg      1320
ggcttccgat ccctgaagga aattagtgct gggcgtatct atataagtgc caataggcag      1380
ctctgctacc accactcttt gaactggacc aaggtgcttc gggggcctac ggaagagcga      1440
ctagacatca agcataatcg gccgcgcaga gactgcgtgg cagagggcaa agtgtgtgac      1500
ccactgtgct cctctggggg atgctgggc ccaggccctg tcagtgctt gtcctgtcga        1560 aattatagcc gaggaggtgt ctgtgtgacc cactgcaact ttctgaatgg ggagcctcga      1620
gaatttgccc atgaggccga atgcttctcc tgccacccgg aatgccaacc catggagggc      1680
actgccacat gcaatggctc gggctctgat acttgtgctc aatgtgccca ttttcgagat      1740
gggccccact gtgtgagcag ctgcccccat ggagtcctag gtgccaaggg cccaatctac      1800
aagtacccag atgttcagaa tgaatgtcgg ccctgccatg agaactgcac ccaggggtgt      1860
aaaggaccag agcttcaaga ctgtttagga caaacactgg tgctgatcgg caaa           1914

<210> SEQ ID NO 5
<211> LENGTH: 475
<212> TYPE: DNA
<213> ORGANISM: Homo sapiens

<400> SEQUENCE: 5
gatcctgtcc tgggactctg aatggcctga gtgtgaccgg cgatgctgag aaccaatacc        60
agacactgta caagctctac gagaggtgtg aggtggtgat ggggaacctt gagattgtgc       120
tcacgggaca caatgccgac ctctccttcc tgcagtggat tcgagaagtg acaggctatg       180
tcctcgtggc catgaatgaa ttctctactc taccattgcc caacctccgc gtggtgcgag       240
ggacccaggt ctacgatggg aagtttgcca tcttcgtcat gttgaactat aacaccaact       300
ccagccacgc tctgcgccag ctccgcttga ctcagctcac cgagattctg tcaggggtg       360 tttatattga gaagaacgat aagctttgtc acatggacac aattgactgg agggacatcg       420
tgagggaccg agatgctgag atagtggtga aggacaatgg cagaagctga ctcga           475

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
tctgcggagt catgagggc                                                     19

<210> SEQ ID NO 7
<211> LENGTH: 48
<212> TYPE: DNA
<213> ORGANISM: Artificial Sequence
<220> FEATURE:
<223> OTHER INFORMATION: Primer

<400> SEQUENCE: 7
tgtgaccacg actagccgtt tctgatgttc ctgctactgc tgttcact                     48

<210> SEQ ID NO 8
<211> LENGTH: 16
<212> TYPE: DNA
```

-continued

<213> ORGANISM: Artificial Sequence
<220> FEATURE:
<223> OTHER INFORMATION: Primer

<400> SEQUENCE: 8
tttctgcgga gtcatg                                                        16

<210> SEQ ID NO 9
<211> LENGTH: 15
<212> TYPE: DNA
<213> ORGANISM: Artificial Sequence
<220> FEATURE:
<223> OTHER INFORMATION: Primer

<400> SEQUENCE: 9
gacgacgacg acaag                                                         15

<210> SEQ ID NO 10
<211> LENGTH: 16
<212> TYPE: DNA
<213> ORGANISM: Artificial Sequence
<220> FEATURE:
<223> OTHER INFORMATION: Primer

<400> SEQUENCE: 10
gccatggctg atatcg                                                        16

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
gcaccaccac caccaccact gag                                                23

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
tggccatgga catcaagcat aatcggcc                                           28

<210> SEQ ID NO 13
<211> LENGTH: 28
<212> TYPE: DNA
<213> ORGANISM: Artificial sequence
<220> FEATURE:
<223> OTHER INFORMATION: Primer

<400> SEQUENCE: 13
gaaagactta cccctcggag agctcgtg                                           28

<210> SEQ ID NO 14
<211> LENGTH: 89
<212> TYPE: PRT
<213> ORGANISM: Homo sapiens

<400> SEQUENCE: 14

Met Lys Tyr Leu Leu Pro Thr Ala Ala Ala Gly Leu Leu Leu Leu Ala
 1               5                  10                  15

Ala Gln Pro Ala Met Ala Met Asp Ile Lys His Asn Arg Pro Arg Arg

```
                20                  25                  30
Asp Cys Val Ala Glu Gly Lys Val Cys Asp Pro Leu Cys Ser Ser Gly
                35                  40                  45

Gly Cys Trp Gly Pro Gly Pro Gly Gln Cys Leu Ser Cys Arg Asn Tyr
        50                  55                  60

Ser Arg Gly Gly Val Cys Val Thr His Cys Asn Phe Leu Asn Gly Glu
65                  70                  75                  80

Pro Leu Glu His His His His His His
                85

<210> SEQ ID NO 15
<211> LENGTH: 456
<212> TYPE: DNA
<213> ORGANISM: Homo sapiens

<400> SEQUENCE: 15
atggtttgtg tagccagctg tccccataac tttgtggtgg atcaaacatc ctgtgtcagg       60
gcctgtcctc ctgacaagat ggaagtagat aaaaatgggc tcaagatgtg tgagccttgt      120 ggggactat gtcccaaagc ctgtgaggga caggctctg ggagccgctt ccagactgtg       180
gactcgagca acattgatgg atttgtgaac tgcaccaaga tcctgggcaa cctggacttt      240
ctgatcaccg gctcaatgg agaccctgg cacaagatcc ctgccctga cccagagaag        300 ctcaatgtct tccggacagt acgggagatc acaggttacc tgaacatcca gtcctggccg      360
ccccacatgc acaacttcag tgttttttcc aatttgacaa ccattggagg cagaaagctt      420
gcggccgcac tcgagcacca ccaccaccac cactga                                456

<210> SEQ ID NO 16
<211> LENGTH: 151
<212> TYPE: PRT
<213> ORGANISM: Homo sapiens

<400> SEQUENCE: 16

Met Val Cys Val Ala Ser Cys Pro His Asn Phe Val Val Asp Gln Thr
1               5                   10                  15

Ser Cys Val Arg Ala Cys Pro Pro Asp Lys Met Glu Val Asp Lys Asn
                20                  25                  30

Gly Leu Lys Met Cys Glu Pro Cys Gly Gly Leu Cys Pro Lys Ala Cys
                35                  40                  45

Glu Gly Thr Gly Ser Gly Ser Arg Phe Gln Thr Val Asp Ser Ser Asn
        50                  55                  60

Ile Asp Gly Phe Val Asn Cys Thr Lys Ile Leu Gly Asn Leu Asp Phe
65                  70                  75                  80

Leu Ile Thr Gly Leu Asn Gly Asp Pro Trp His Lys Ile Pro Ala Leu
                85                  90                  95

Asp Pro Glu Lys Leu Asn Val Phe Arg Thr Val Arg Glu Ile Thr Gly
                100                 105                 110

Tyr Leu Asn Ile Gln Ser Trp Pro Pro His Met His Asn Phe Ser Val
            115                 120                 125

Phe Ser Asn Leu Thr Thr Ile Gly Gly Arg Ser Lys Leu Ala Ala Ala
        130                 135                 140

Leu Glu His His His His His His
145                 150

<210> SEQ ID NO 17
<211> LENGTH: 270
<212> TYPE: DNA
```

```
<213> ORGANISM: Homo sapiens

<400> SEQUENCE: 17
atgaaatacc tgctgccgac cgctgctgct ggtctgctgc tcctcgctgc ccagccggcg      60
atggccatgg acatcaagca taatcggccg cgcagagact gcgtggcaga gggcaaagtg     120
tgtgacccac tgtgctcctc tgggggatgc tggggcccag gccctggtca gtgcttgtcc     180
tgtcgaaatt atagccgagg aggtgtctgt gtgacccact gcaactttct gaatggggag     240
cccctcgagc accaccacca ccaccactga                                      270
```

ERBB-3 BASED METHODS AND COMPOSITIONS FOR TREATING NEOPLASMS

CROSS-REFERENCE TO RELATED APPLICATIONS

The present application is a national phase of PCT/CN03/00217, having an international filing date of Mar. 26, 2003, which claims priority from the Chinese Patent Application No. 02116259.x, filed Mar. 26, 2002. The disclosures of the above applications are incorporated by reference in their entireties.

Technical Field

The present invention relates to compositions and methods for treating neoplasms in mammals, particularly humans. More particularly, the present invention provides for methods for preventing, treating or delaying neoplasm in a mammal using an ErbB-3 protein, a nucleic acid encoding an ErbB-3 protein or a functional fragment thereof. The present invention also provides for isolated nucleic acids encoding an extracellular domain of the ErbB-3 protein, or a functional fragment thereof, substantially purified extracellular domain of the ErbB-3 protein, or a functional fragment thereof and antibodies that bind to an epitope in an extracellular domain of the ErbB-3 protein, or a functional fragment thereof. The present invention further provides for pharmaceutical compositions and/or vaccines comprising the extracellular domain of the ErbB-3 protein, or a functional fragment thereof, or nucleic acids encoding and antibodies binding to such extracellular domain or functional fragments thereof.

Background Art

Cancer is a major lethal disease for humans and is caused by physiologically-uncontrolled cell proliferation which affects normal physiological conditions of human body resulting in serious pathological reactions often leading to death. Although tremendous efforts on cancer studies and treatments have been made, presently, cancer is still the major cause of death to humans. There are multiple approaches to treat cancer patients including surgery, radiation therapy and chemotherapy. As the first two methods are not able to completely eliminate cancer cells in patients, the latter approach is commonly used to control cancer cell growth with or without other treatments. Anti-cancer compounds used in patients are often targeting prevention of cancer cell proliferation or killing dividing cells.

When the compounds are toxic to cancer cells, they may also severely affect normal dividing cells which are necessary for human life. Therefore, one of main directions in cancer studies is to find methods to specifically block or kill cancer cells without affecting normal cell proliferation. There is a demand now for such treatment on cancer patients.

ErbBs are class one receptor protein tyrosine kinases. ErbB-mediated cell signaling plays a critical role in embryo development and adult organ function. On a cellular level, ErbB receptors have been shown to mediate signals for cell proliferation, differentiation, migration, and cell structure reorganization. There are four structurally similar ErbB members, ErbB-1, ErbB-2 . ErbB-3 and ErbB-4 . The epidermal growth factor (EGF) is one of several ligands that bind ErbB-1 . ErbB-3 or ErbB-4 also bind several ligands, including neuregulin-1 (NRG-1). To date, no ligand for ErbB-2 has been identified. However, ErbB-2 serves as a heterodimer partner for ErbB-3, ErbB-4 or ErbB-1 and is critically involved in NRG-1-activated cell signaling.

In vivo studies using gene targeting experiments indicate that developmental defects resulting from inactivation of ErbB-2 are similar to those observed in NRG-1-inactivated animals. Both animals show defects in the neural crania ganglia and heart trabeculae development. Furthermore, ErbB-3 or ErbB-4 gene-inactivated mice have similar or overlapping phenotypes to NRG-1 or ErbB-2 knockout mice.

In addition to its role in development, the human ErbB-2 gene is frequently amplified and its encoded protein is overexpressed in a variety of human carcinomas. Early research on ErbB-2 discovered that an oncogenic point mutation resulted in the formation of ErbB-2 homodimers that in turn caused significant phosphorylation of the tyrosine residues on the intracellular domain. While no corresponding point mutation has been found in ErbB-2 over expressing human carcinomas, the upregulation of ErbB-2 results in the formation of homodimers that in turn increases the tyrosine phosphorylation of its intracellular domain. This process is hypothesized to be the start of a signal cascade that triggers cell transformation and/or growth, and thus initiate tumorigenesis. There is evidence, however, to contradict the hypothesis that ErbB-2 homodimers are responsible for the initiation of tumorigenesis: i) some ErbB-2 mutants that are engineered to enhanced dimerization and self-phosphorylation have no effect on cell transformation ; ii) antibodies that bind to the extracellular domain of ErbB-2 and presumably promote homodimerization result in ErbB2-expressing cancer cell growth promotion, whereas others inhibit cancer cell growth. These data indicate that homodimerization of ErbB-2 is insufficient for cell growth promotion or cell transformation, and other conditions, possibly involving specific dimer orientation or conformation, are required.

ErbB-2 acts as a heterodimer partner for the ligand-binding ErbB-3 or ErbB-4 receptors. The ligand, NRG-1, has been identified to have two independent receptor binding sites: one that has a high affinity for ErbB-3 or ErbB-4, and the other that has a low but non-specific affinity for all ErbB members. Thus, the exposure of NRG-1 to cells expressing ErbB-3/4 and ErbB-2 would result in heterodimers of ErbB-2 and ErbB-3/4. In the absence of the ligand, however, it is unclear whether ErbB-2 has an affinity with other ErbB receptors, and it is possible that such an interaction could be involved in the initiation of cancer. Amongst all the ErbB receptors, ErbB-3 is unique because: i) ErbB-2 preferentially forms heterodimers with ErbB-3; ii) cotransfection of NIH3T3 cells with ErbB-2 and ErbB-3 results in much higher levels of cell transformation than that of transfection with ErbB-2 alone; iii) in ErbB-2 over-expression-associated breast cancer cells, ErbB-3 is also highly expressed; and iv) ErbB-3 is also over expressed in ErbB-2-over expressing tumour cells from ErbB-2 transgenic mice.

A number of patents and patent applications disclose ErbB-2 and/or ErbB-3 related neoplasm or cancer treatment. For example, WO 00/78347 discloses methods for arresting or inhibiting cell growth, particularly cancer cell growth, comprising preventing or reducing ErbB-2/ErbB-3 heterodimer formation, or interfering with ErbB-2/ErbB-3 heterodimer conformation in a cell and agents which prevent or reduce ErbB-2/ErbB-3 heterodimer formation or interfere with ErbB-2/ErbB-3 heterodimer conformation in a cell thereby arresting or inhibiting the growth of the cell. U.S. Pat. No. 5,578,482 relates to erbB-2 ligands and functional derivatives thereof which are capable of binding to the erbB-2 oncogene product. U.S. Pat. No. 5,820,859 relates to a method of targeting a therapeutic agent to cells expressing the erb B-3 receptor. U.S. Pat. No. 5,968,511 relates to ErbB3 antibodies.

There exists a need in the art for more efficient and/or cost effective ErbB-3 related neoplasm treatments. The present invention addresses this and other related needs in the art.

DISCLOSURE OF THE INVENTION

In one aspect, the present invention is directed to a method for preventing, treating or delaying neoplasm in a mammal, which method comprises administering to a mammal, to which such prevention, treatment or delay is needed or desirable, an effective amount of an ErbB-3 protein, or a functional fragment thereof, or a nucleic acid encoding an ErbB-3 protein, or a functional fragment thereof, whereby an immune response is generated against said neoplasm and said neoplasm is prevented, treated or delayed.

In another aspect, the present invention is directed to an isolated nucleic acid fragment, which isolated nucleic acid fragment comprises a sequence of nucleotides encoding an extracellular domain of the ErbB-3 protein, or a functional fragment thereof, comprising an amino acid sequence set forth in SEQ ID NO:2 (FIG. 5) or SEQ ID NO:3 (FIG. 11) or an amino acid sequence comprising at least amino acid residues 24-81 of the amino acid sequence set forth in SEQ ID NO:14 or an amino acid sequence comprising at least amino acid residues 2-139 of the amino acid sequence set forth in SEQ ID NO:16.

In still another aspect, the present invention is directed to a substantially purified protein or peptide, which comprises an extracellular domain of the ErbB-3 protein, or a functional fragment thereof, comprising an amino acid sequence set forth in SEQ ID NO:2 or SEQ ID NO:3 or an amino acid sequence comprising at least amino acid residues 24-81 of the amino acid sequence set forth in SEQ ID NO:14; or an amino acid sequence comprising at least amino acid residues 2-139 of the amino acid sequence set forth in SEQ ID NO:16.

In yet another aspect, the present invention is directed to a conjugate, which conjugate comprises: a) a protein or peptide comprising an extracellular domain of the ErbB-3 protein, or a functional fragment thereof, comprising an amino acid sequence set forth in SEQ ID NO:2 or SEQ ID NO:3 or an amino acid sequence comprising at least amino acid residues 24-81 of the amino acid sequence set forth in SEQ ID NO:14; or an amino acid sequence comprising at least amino acid residues 2-139 of the amino acid sequence set forth in SEQ ID NO:16.; and b) a facilitating agent linked to the extracellular domain of the ErbB-3 protein, or a functional fragment thereof, directly or via a linker, wherein the agent facilitates: i) affinity isolation or purification of a conjugate; ii) attachment of a conjugate to a surface; or iii) detection of a conjugate.

In yet another aspect, the present invention is directed to an antibody, which antibody binds to an epitope in an extracellular domain of the ErbB-3 protein, or a functional fragment thereof, comprising an amino acid sequence set forth in SEQ ID NO:2 or SEQ ID NO:3 or an amino acid sequence comprising at least amino acid residues 24-81 of the amino acid sequence set forth in SEQ ID NO:14; or an amino acid sequence comprising at least amino acid residues 2-139 of the amino acid sequence set forth in SEQ ID NO:16.

Pharmaceutical compositions and/or vaccines comprising the extracellular domain of the ErbB-3 protein, or a functional fragment thereof, or nucleic acids encoding and antibodies binding to such extracellular domain or functional fragments thereof are also provided.

BRIEF DESCRIPTION OF THE DRAWINGS

FIG. 1 depicts B3 cDNA sequence (SEQ ID NO:4).

FIG. 5 depicts B3 amino acid sequence (SEQ ID NO:2).

FIG. 6 depicts DE3-1 cDNA sequence (SEQ ID NO:5).

FIG. 11 depicts DE3-1 amino acid sequence (SEQ ID NO:3).

FIG. 22 illustrates Experimental results of anti-tumor effect of rhErbB3-f78.

FIG. 23 depicts ErbB3-f12 amino acid sequence (SEQ ID NO: 14) and cDNA sequence (SEQ ID NO:17).

FIG. 24 depicts ErbB3-f78 cDNA sequence (SEQ ID NO:15).

FIG. 25 depicts ErbB3-f78 amino acid sequence (SEQ ID NO:16).

MODES OF CARRYING OUT THE INVENTION

Figure 2:
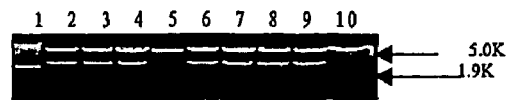
FIG. 2 illustrates restriction enzyme digestion of B3 plasmid. Lane 1:1 KB ladder (NEB). Lane2-9: DNA for diagnostic digestion with BamHI/XbaI. All are correct clones except the colony on Lane 5. Lane10: pCDNA3 vector alone digested with BamHI/XbaI.
Figure 3:
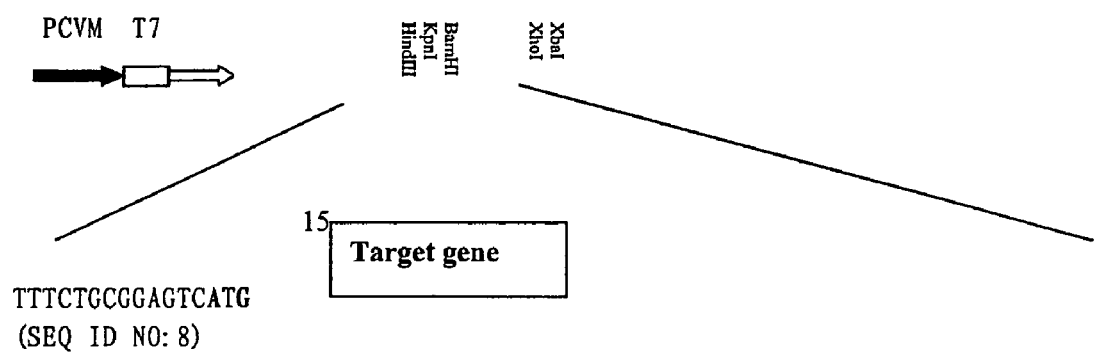
FIG. 3 illustrates B3 plasmid construction.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "neoplasm (neoplasia)" refers to abnormal new growth, and thus means the same as tumor, which may be benign or malignant. Unlike hyperplasia, neoplastic proliferation persists even in the absence of the original stimulus.

As used herein, "cancer" refers to a general term for diseases caused by any type of malignant tumor.

As used herein, "malignant," as applies to tumors, refers to primary tumors that have the capacity of metastasis with loss of both growth control and positional control.

As used herein, "erb" refers to two oncogenes, erb A and erb B, associated with erythroblastosis virus (an acute transforming retrovirus).

As used herein, "immune response" refers to alteration in the reactivity of an organism's immune system in response to an antigen; in vertebrates, this may involve antibody production, induction of cell-mediated immunity, complement activation or development of immunological tolerance.

As used herein, "immune response potentiator" refers to a substance that enhances an antigen's effect in eliciting an immune response.

As used herein, "vaccine" refers to any compositions intended for active immunological prophylaxis. A vaccine may be used therapeutically to treat a disease, or to prevent development of a disease or to decrease the severity of a disease either proactively or after infection. Exemplary vaccines include, but are not limited to, preparations of killed microbes of virulent strains or living microbes of attenuated (variant or mutant) strains, or microbial, fungal, plant, protozoa, or metazoa derivatives or products. "Vaccine" also encompasses protein/peptide and nucleic acid/oligonucleotides based vaccines.

As used herein, "anti-neoplasm agent (used interchangeably with anti-neoplastic agent, anti-tumor or anti-cancer agent)" refers to any agents used in the anti-neoplasm treatment. These include any agents, that when used alone or in combination with other compounds, can alleviate, reduce, ameliorate, prevent, or place or maintain in a state of remission of clinical symptoms or diagnostic markers associated with neoplasm, tumor or cancer, and can be used in methods, combinations and compositions provided herein. Anti-neoplastic agents include, but are not limited to, anti-angiogenic agents, alkylating agents, antimetabolite, certain natural products, platinum coordination complexes, anthracenediones, substituted ureas, methylhydrazine derivatives, adrenocortical suppressants, certain hormones and antagonists, anti-cancer polysaccharides and certain herb extracts such as Chinese herb extracts.

As used herein, an "anti-neoplastic treatment" refers to any treatment designed to treat the neoplasm, tumor or cancer by lessening or ameliorating its symptoms. Treatments that prevent the occurrence of neoplasm, tumor or cancer or lessen its severity are also contemplated.

As used herein, "anti-neoplasm agent (or anti-tumor or anti-cancer agent) or anti-neoplasm treatment" does not encompass an ErbB-3 protein, or a functional fragment thereof, or a nucleic acid encoding an ErbB-3 protein, or a functional fragment thereof, or use thereof for treatment, but encompasses all agents and treatment modalities known to those of skill in the art to ameliorate the symptoms in some manner of a neoplasm, tumor or cancer.

As used herein, "an effective amount of a compound for treating a particular disease" is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, "treatment" means any manner in which the symptoms of a conditions, disorder or disease are ameliorated or otherwise beneficially altered. Treatment also encompasses any pharmaceutical use of the compositions herein.

As used herein, "amelioration" of the symptoms of a particular disorder by administration of a particular pharmaceutical composition refers to any lessening, whether permanent or temporary, lasting or transient that can be attributed to or associated with administration of the composition.

As used herein, "antibody" is used in the broadest sense and specifically covers intact monoclonal antibodies, polyclonal antibodies, multi-specific antibodies, e.g., bi-specific antibodies, formed from at least two intact antibodies, and antibody fragments so long as they exhibit the desired biological activity. The antibody may be an IgM, IgG, e.g., $IgG_1$, $IgG_2$, $IgG_3$ or $IgG_4$, IgD, IgA or IgE, for example.

As used herein, "antibody fragments" comprise a portion of an intact antibody, generally the antigen binding or variable region of the intact antibody. Examples of antibody fragments include Fab, Fab', $F(ab')_2$, and Fv fragments; diabodies; single-chain antibody molecules; and multi-specific antibodies formed from antibody fragments.

As used herein, "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins.

As used herein, "polyclonal antibody" refers to antibodies produced by several clones of B-lymphocytes as would be the case in a whole animal. Usually refers to antibodies raised in immunized animals, whereas a monoclonal antibody is the product of a single clone of B-lymphocytes, usually maintained in vitro.

As used herein, "hybridoma" refers to a cell hybrid in which a tumour cell forms one of the original source cells. Exemplary hybridoma are hybrids between T- or B-lymphocytes and appropriate myeloma cell lines that produce a monoclonal antibody.

As used herein, "humanized antibodies" refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, "production by recombinant means" refers to production methods that use recombinant nucleic acid methods that rely on well known methods of molecular biology for expressing proteins encoded by cloned nucleic acids.

As used herein, "complementary" when referring to two nucleic acid molecules, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: "stringency of hybridization" in determining percentage mismatch is as follows:
1) high stringency: 0.1×SSPE, 0.1% SDS, 65 ⁰C;
2) medium stringency: 0.2×SSPE, 0.1% SDS, 50 ⁰C (also referred to as moderate stringency); and
3) low stringency: 1.0×SSPE, 0.1% SDS, 50 ⁰C.
It is understood that equivalent stringencies may be achieved using alternative buffers, salts and temperatures.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, J. Biol. Chem., 266: 19867-19870 (1991)) can be inserted immediately 5' of the start codon and may enhance expression. The desirability of (or need for) such modification may be empirically determined.

As used herein, "protein binding sequence" refers to a protein or peptide sequence that is capable of specific binding to other protein or peptide sequences generally, to a set of protein or peptide sequences or to a particular protein or peptide sequence.

As used herein, "epitope tag" refers to a short stretch of amino acid residues corresponding to an epitope to facilitate subsequent biochemical and immunological analysis of the "epitope tagged" protein or peptide. "Epitope tagging" is achieved by appending the sequence of the "epitope tag" to the protein-encoding sequence in an appropriate expression vector. "Epitope tagged" proteins can be affinity purified using highly specific antibodies raised against the tags.

As used herein, "Protein A or Protein G" refers to proteins that can bind to Fc region of most IgG isotypes. Protein A or Protein G are typically found in the cell wall of some strains of staphylococci. It is intended to encompass Protein A or Protein G with conservative amino acid substitutions that do not substantially alter its activity.

As used herein, "nucleotide binding sequence" refers to a protein or peptide sequence that is capable of specific binding to nucleotide sequences generally, to a set of nucleotide sequences or to a particular nucleotide sequence.

As used herein, "lipid binding sequence" refers to a protein or peptide sequence that is capable of specific binding to lipids generally, to a set of lipids or to a particular lipid.

As used herein, "polysaccharide binding sequence" refers to a protein or peptide sequence that is capable of specific binding to polysaccharides generally, to a set of polysaccharides or to a particular polysaccharide.

As used herein, "metal binding sequence" refers to a protein or peptide sequence that is capable of specific binding to metal ions generally, to a set of metal ions or to a particular metal ion.

B. Methods for Preventing, Treating or Delaying Neoplasm Using ErbB-3

In one aspect, the present invention is directed to a method for preventing, treating or delaying neoplasm in a mammal, which method comprises administering to a mammal, to which such prevention, treatment or delay is needed or desirable, an effective amount of an ErbB-3 protein, or a functional fragment thereof, or a nucleic acid encoding an ErbB-3 protein, or a functional fragment thereof, whereby an immune response is generated against said neoplasm and said neoplasm is prevented, treated or delayed.

The present method can be used for preventing, treating or delaying neoplasm in any mammals, such as mice, rats, rabbits, cats, dogs, pigs, cows, ox, sheep, goats, horses, monkeys and other non-human primates. Preferably, the present method can be used for preventing, treating or delaying neoplasm in humans.

Any suitable ErbB-3 protein, or a functional fragment thereof, or a nucleic acid encoding an ErbB-3 protein, or a functional fragment thereof, that can elicit an immune response to the neoplasm to be treated, prevented or delayed, can be used in the present method. The ErbB-3 elicited immune response can be cellular, humoral or both. For example, ErbB-3 protein, or a functional fragment thereof, or a nucleic acid encoding an ErbB-3 protein, or a functional fragment thereof, disclosed in U.S. Pat. No. 5,820,859 can be used in the present method. In other examples, ErbB-3 protein, or a functional fragment thereof, or a nucleic acid encoding an ErbB-3 protein, or a functional fragment thereof, derived from rat ErbB-3 (GenBank Accession No. U29339; and Hellyer et al., *Gene*, 165(2:279-284 (1995)), Fugu rubripes ErbB-3 (GenBank Accession No. AF056116; and Gellner and Brenner, *Genome Res.*, 9(3):251-258 (1999)) and human ErbB-3 (GenBank Accession No. M29366; and Kraus et al., *Proc. Natl. Acad. Sci. U.S.A.*, 86:9193-9197 (1989)) can be used in the present method. Preferably, ErbB-3 protein, or a functional fragment thereof, or a nucleic acid encoding an ErbB-3 protein, or a functional fragment thereof, derived from human ErbB-3 is used in the present method. Any ErbB-3 protein, or a functional fragment thereof, with conservative amino acid substitutions that do not substantially alter its activity can be used in the present method.

In a preferred embodiment, an effective amount of an extracellular domain of an ErbB-3 protein, or a functional fragment thereof, or a nucleic acid encoding an extracellular domain of an ErbB-3 protein, or a functional fragment thereof, is administered. In another preferred embodiment, an effective amount of the ErbB-3 protein comprising an amino acid sequence set forth in SEQ ID NO:1 or at least amino acid residues 24-81 of the amino acid sequence set forth in SEQ ID NO:14, or at least amino acid residues 2-139 of the amino acid sequence set forth in SEQ ID NO:16 is administered. In still another preferred embodiment, an effective amount of the extracellular domain of the ErbB-3 protein, or a functional fragment thereof, comprising an amino acid sequence set forth in SEQ ID NO:2 or SEQ ID NO:3, is administered.

The present method can further comprise administering an immune response potentiator to the mammal. The immune response potentiator can be administered prior to, concurrently with, or subsequent to the administration of the ErbB-3 protein, or a functional fragment thereof, or a nucleic acid an ErbB-3 protein, or a functional fragment thereof. Exemplary immune response potentiators include Bacille Calmette-Guerin (BCG) (Ratliff, *Eur. Urol.*, 2:17-21 (1992)), Corynebacterium Parvum (Lillehoj et al., *Avian Dis.*, 37(3 :731-40 (1993)), *Brucella abortus* extract, glucan, levamisole, tilorone, an enzyme, a non-virulent virus, polysaccharides, and herb extracts such as Chinese herb extracts.

The formulation, dosage and route of administration of ErbB-3 protein, or a functional fragment thereof, or a nucleic acid encoding an ErbB-3 protein, or a functional fragment thereof, preferably in the form of pharmaceutical compositions, can be determined according to the methods known in the art (see e.g., *Remington: The Science and Practice of Pharmacy*, Alfonso R. Gennaro (Editor) Mack Publishing Company, April 1997; *Therapeutic Peptides and Proteins: Formulation, Processing, and Delivery Systems*, Banga, 1999; and *Pharmaceutical Formulation Development of Peptides and Proteins*, Hovgaard and Frkjr (Ed.), Taylor & Francis, Inc., 2000; *Medical Applications of Liposomes*, Lasic and Papahadjopoulos (Ed.), Elsevier Science, 1998; *Textbook of Gene Therapy*, Jain, Hogrefe & Huber Publishers, 1998; *Adenoviruses: Basic Biology to Gene Therapy*, Vol. 15, Seth, Landes Bioscience, 1999; *Biopharmaceutical Drug Design and Development*, Wu-Pong and Rojanasakul (Ed.), Humana Press, 1999; *Therapeutic Angiogenesis: From Basic Science to the Clinic*, Vol. 28, Dole et al. (Ed.), Springer-Verlag New York, 1999). The ErbB-3 protein, or a functional fragment thereof, or a nucleic acid encoding an ErbB-3 protein, or a functional fragment thereof, can be formulated for oral, rectal, topical, inhalational, buccal (e.g., sublingual), parenteral (e.g., subcutaneous, intramuscular, intradermal, or intravenous), transdermal administration or any other suitable route of administration. The most suitable route in any given case will depend on the nature and severity of the condition being treated and on the nature of the particular ErbB-3 protein, or a functional fragment thereof, or a nucleic acid encoding an ErbB-3 protein, or a functional fragment thereof, which is being used.

The ErbB-3 protein, or a functional fragment thereof, or a nucleic acid encoding an ErbB-3 protein, or a functional fragment thereof, can be administered to any suitable place in the mammal. Preferably, the ErbB-3 protein, or a functional fragment thereof, or a nucleic acid encoding an ErbB-3 protein, or a functional fragment thereof, is administered to the neoplasm in situ, i.e., administered to the place where the neoplasm is located or the vicinity thereof. Also, preferably, the present method can further comprise administering an immune response potentiator to the neoplasm in situ.

The ErbB-3 protein, or a functional fragment thereof, or a nucleic acid encoding an ErbB-3 protein, or a functional fragment thereof, can be administered alone. Alternatively and preferably, the ErbB-3 protein, or a functional fragment thereof, or a nucleic acid encoding an ErbB-3 protein, or a functional fragment thereof, is co-administered with a pharmaceutically acceptable carrier or excipient. Any suitable pharmaceutically acceptable carrier or excipient can be used in the present method (See e.g., *Remington: The Science and Practice of Pharmacy*, Alfonso R. Gennaro (Editor) Mack Publishing Company, April 1997).

The present method can be used alone. Alternatively, the present method can be used in combination with other anti-neoplasm treatment, e.g., radiationtherapy, chemotherapy or surgery. The present method can also be used in combination with other anti-neoplasm agent. Such other anti-neoplasm treatment or agent can be used before, with or after the administration of ErbB-3 protein, or a functional fragment thereof, or a nucleic acid encoding an ErbB-3 protein, or a functional fragment thereof. For example, the ErbB-3 protein, or a functional fragment thereof, or a nucleic acid encoding an ErbB-3 protein, or a functional fragment thereof, can be co-administered with an anti-neoplasm agent.

Any suitable anti-neoplasm agent can be used in the present method. Exemplary anti-neoplasm agents include an anti-angiogenic agent (See e.g. Auerbach and Auerbach, *Pharmacol. Ther.*, 63(3):265-311 (1994)), an alkylating agent, an antimetabolite, a natural product, a platinum coordination complex, an anthracenedione, a substituted urea, a methylhydrazine derivative, an adrenocortical suppressant, a hormone, an antagonist, an oncogene inhibitor, a tumor suppressor gene or protein, an anti-oncogene antibody and an anti-oncogene antisense oligonucleotide.

The nucleic acid encoding an ErbB-3 protein, or a functional fragment thereof, or any tumor suppressor gene can be used in the form of naked DNA, complexed DNA, cDNA, plasmid DNA, RNA or other mixtures thereof as components of the gene delivery system. In another embodiment, the nucleic acid encoding an ErbB-3 protein, or a functional fragment thereof, or the tumor suppressor gene is included in a viral vector. Any viral vectors that are suitable for gene therapy can used in the combination. For example, an adenovirus vector (U.S. Pat. No. 5,869,305), a simian virus vector (U.S. Pat. No. 5,962,274), a conditionally replicating human immunodeficiency viral vector (U.S. Pat. No. 5,888,767), retrovirus, SV40, Herpes simplex viral amplicon vectors and Vaccinia virus vectors can be used. In addition, the genes can be delivered in a non-viral vector system such as a liposome wherein the lipid protects the DNA or other biomaterials from oxidation during the coagulation.

The present method can be used to treat, prevent or delay any suitable neoplasms or cancers. Preferably, the present method is used to treat, prevent or delay any suitable neoplasms or cancers wherein the interaction between ErbB-2 and ErbB-3 is critical for causing or sustaining the neoplasms or cancers. For example, the present method can be used to treat, prevent or delay adrenal gland, anus, auditory nerve, bile ducts, bladder, bone, brain, breast, bruccal, central nervous system, cervix, colon, ear, endometrium, esophagus, eye, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve and vulva neoplasm. Preferably, the present method is used to treat, prevent or delay breast, ovary, stomach, prostate, colon and lung cancer. More preferably, the present method is used to treat, prevent or delay breast cancer.

According to the present invention, the ErbB-3 protein, or a functional fragment thereof, or a nucleic acid encoding an ErbB-3 protein, or a functional fragment thereof, alone or in combination with other agents, carriers or excipients, may be formulated for any suitable administration route, such as intracavernous injection, subcutaneous injection, intravenous injection, intramuscular injection, intradermal injection, oral or topical administration. The method may employ formulations for injectable administration in unit dosage form, in ampoules or in multidose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, sterile pyrogen-free water or other solvents, before use. Topical administration in the present invention may employ the use of a foam, gel, cream, ointment, transdermal patch, or paste.

Pharmaceutically acceptable compositions and methods for their administration that may be employed for use in this invention include, but are not limited to those described in U.S. Pat. Nos. 5,736,154; 6,197,801 B1; 5,741,511; 5,886,039; 5,941,868; 6,258,374 B1; and 5,686,102.

The magnitude of a therapeutic dose in the treatment or prevention will vary with the severity of the condition to be treated and the route of administration. The dose, and perhaps dose frequency, will also vary according to age, body weight, condition and response of the individual patient.

It should be noted that the attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

Any suitable route of administration may be used. Dosage forms include tablets, troches, cachet, dispersions, suspensions, solutions, capsules, patches, and the like. See, Remington's Pharmaceutical Sciences.

In practical use, the ErbB-3 protein, or a functional fragment thereof, or a nucleic acid encoding an ErbB-3 protein, or a functional fragment thereof, alone or in combination with other agents, may be combined as the active in intimate admixture with a pharmaceutical carrier or excipient, such as beta-cyclodextrin and 2-hydroxy-propyl-beta-cyclodextrin, according to conventional pharmaceutical compounding techniques. The carrier may take a wide form of preparation desired for administration, topical or parenteral. In preparing compositions for parenteral dosage form, such as intravenous injection or infusion, similar pharmaceutical media may be employed, water, glycols, oils, buffers, sugar, preservatives, liposomes, and the like known to those of skill in the art. Examples of such parenteral compositions include, but are not limited to dextrose 5% w/v, normal saline or other solutions. The total dose of the ErbB-3 protein, or a functional fragment thereof, or a nucleic acid encoding an ErbB-3 protein, or a functional fragment thereof, alone or in combination with other agents to be administered may be administered in a vial of intravenous fluid, ranging from about 1 ml to 2000 ml. The volume of dilution fluid will vary according to the total dose administered.

The invention also provides for kits for carrying out the therapeutic regimens of the invention. Such kits comprise in one or more containers therapeutically effective amounts of the ErbB-3 protein, or a functional fragment thereof, or a nucleic acid encoding an ErbB-3 protein, or a functional fragment thereof, alone or in combination with other agents, in pharmaceutically acceptable form. Preferred pharmaceutical forms would be in combination with sterile saline, dextrose solution, or buffered solution, or other pharmaceutically acceptable sterile fluid. Alternatively, the composition may be lyophilized or dessicated; in this instance, the kit optionally further comprises in a container a pharmaceutically acceptable solution, preferably sterile, to reconstitute the complex to form a solution for injection purposes. Exemplary pharmaceutically acceptable solutions are saline and dextrose solution.

In another embodiment a kit of the invention further comprises a needle or syringe, preferably packaged in sterile form, for injecting the composition, and/or a packaged alcohol pad. Instructions are optionally included for administration of composition by a physician or by the patient.

C. Extracellular Domains of the ErbB-3 Protein and Nucleic Acids Encoding the Extracellular Domains of the ErbB-3 Protein and Uses Thereof In another aspect, the present invention is directed to an isolated nucleic acid fragment, which isolated nucleic acid fragment hybridizes, under low, middle or high stringency, with a sequence of nucleotides, or a complementary strand thereof, encoding an extracellular domain of the ErbB-3 protein, or a functional fragment thereof, comprising an amino acid sequence set forth in SEQ ID NO:2 or SEQ ID NO:3 an amino acid sequence comprising at least amino acid residues 24-81 of the amino acid sequence set forth in SEQ ID NO:14; or an amino acid sequence comprising at least amino acid residues 2-139 of the amino acid sequence set forth in SEQ ID NO:16.

In a preferred embodiment, the isolated nucleic acid fragment hybridizes, under high stringency, with a sequence of nucleotides, or a complementary strand thereof, encoding an extracellular domain of the ErbB-3 protein, or a functional fragment thereof, comprising an amino acid sequence set forth in SEQ ID NO:2 or SEQ ID NO:3 an amino acid sequence comprising at least amino acid residues 24-81 of the amino acid sequence set forth in SEQ ID NO:14; or an amino acid sequence comprising at least amino acid residues 2-139 of the amino acid sequence set forth in SEQ ID NO:16. In another preferred embodiment, the isolated nucleic acid fragment comprises a sequence of nucleotides, or a complementary strand thereof, encoding an extracellular domain of the ErbB-3 protein, or a functional fragment thereof, comprising an amino acid sequence set forth in SEQ ID NO:2 or SEQ ID NO:3 an amino acid sequence comprising at least amino acid residues 24-81 of the amino acid sequence set forth in SEQ ID NO:14; or an amino acid sequence comprising at least amino acid residues 2-139 of the amino acid sequence set forth in SEQ ID NO:16. In still another preferred embodiment, the isolated nucleic acid fragment comprises a sequence of nucleotides, or a complementary strand thereof, set forth in SEQ ID NO:4 (FIG. 1) or SEQ ID NO:5 (FIG. 6) or an amino acid sequence comprising at least amino acid residues 24-81 of the amino acid sequence set forth in SEQ ID NO:14; or an amino acid sequence comprising at least amino acid residues 2-139 of the amino acid sequence set forth in SEQ ID NO:16.

The isolated nucleic acid fragments can be in any suitable form. For example, the isolated nucleic acid fragment can comprise DNA, RNA, PNA or a derivative thereof. Alternatively, the isolated nucleic acid fragment can comprise both DNA and RNA or derivatives thereof. The isolated nucleic acid fragment can be single-stranded and be ready to be used in a hybridization analysis. Alternatively, the isolated nucleic acid fragment can be double-stranded and be denatured into single-stranded prior to the hybridization analysis.

The isolated nucleic acid fragment can comprise any kind of oligonucleotide or nucleic acid strand(s) containing genetically-coded and/or naturally occurring structures. The isolated nucleic acid fragments can comprise non-natural elements such as non-natural bases, e.g., inosine and xanthine, non-natural sugars, e.g., 2'-methoxy ribose, or non-natural phosphodiester linkages, e.g., methylphosphonates, phosphorothioates and peptides.

The isolated nucleic acid fragments can be produced by any suitable methods. For example, the isolated nucleic acid fragments can be chemically synthesized (See generally, Ausubel (Ed.) *Current Protocols in Molecular Biology*, 2.11. *Synthesis and purification of oligonucleotides*, John Wiley & Sons, Inc. (2000)), isolated from a natural source, produced by recombinant methods or a combination thereof. Preferably, the isolated nucleic acid fragments are produced by recombinant methods.

The isolated nucleic acid fragment can be labeled for various purposes, e.g., facilitating detection, purification and/or attachment to a surface. The label can be a chemical, an enzymatic, an immunogenic, a radioactive, a fluorescent, a luminescent or a FRET label.

A plasmid, which plasmid comprises the above nucleic acid fragment is also provided. A cell, which cell comprises the above plasmid is further provided. Any suitable cells can be used, e.g., bacterial cells, yeast cells, fungal cells, plant cells, insect cells, animal cells and human cells.

In still another aspect, the present invention is directed to a method for producing an extracellular domain of the ErbB-3 protein, or a functional fragment thereof, which method comprises growing the above cells under conditions whereby the extracellular domain of the ErbB-3 protein, or a functional fragment thereof, is expressed by the cells, and recovering the expressed extracellular domain of the ErbB-3 protein, or a functional fragment thereof.

In yet another aspect, the present invention is directed to a substantially purified protein or peptide, which comprises an extracellular domain of the ErbB-3 protein, or a functional fragment thereof, comprising an amino acid sequence set forth in SEQ ID NO:2 or SEQ ID NO:3 an amino acid sequence comprising at least amino acid residues 24-81 of the amino acid sequence set forth in SEQ ID NO:14; or an amino acid sequence comprising at least amino acid residues 2-139 of the amino acid sequence set forth in SEQ ID NO:16 The extracellular domain of the ErbB-3 protein, or a functional fragment thereof, can be produced by any suitable methods. For example, the extracellular domain of the ErbB-3 protein, or a functional fragment thereof can be chemically synthesized, isolated from a natural source, produced by recombinant methods or a combination thereof. Preferably, the extracellular domains of the ErbB-3 protein, or functional fragments thereof, are produced by recombinant methods.

In yet another aspect, the present invention is directed to a conjugate, which conjugate comprises: a) a protein or peptide comprising an extracellular domain of the ErbB-3 protein, or a functional fragment thereof, comprising an amino acid sequence set forth in SEQ ID NO:2 or SEQ ID NO:3; an amino acid sequence comprising at least amino acid residues 24-81 of the amino acid sequence set forth in SEQ ID NO:14; or an amino acid sequence comprising at least amino acid residues 2-139 of the amino acid sequence set forth in SEQ ID NO:16; and b) a facilitating agent linked to the extracellular domain of the ErbB-3 protein, or a functional fragment thereof, directly or via a linker, wherein the agent facilitates: i) affinity isolation or purification of a conjugate; ii) attachment of a conjugate to a surface; or iii) detection of a conjugate. The conjugate can be a fusion protein. Alternatively, the ErbB-3 protein, or a functional fragment thereof, and the facilitating agent can be linked by other means. When the conjugate is a fusion protein, a nucleic acid encoding the conjugate is also provided.

The conjugates can be produced by chemical conjugation, such as via thiol linkages, but are preferably produced by recombinant means as fusion proteins. In the fusion protein, the peptide or fragment thereof is linked to either the N-terminus or C-terminus of the ErbB-3 protein, or a functional fragment thereof. In chemical conjugates the peptide or fragment thereof may be linked anywhere that conjugation can be effected, and there may be a plurality of such peptides or fragments linked to a single the ErbB-3 protein, or a functional fragment thereof, or to a plurality thereof.

Conjugation can be effected by any method known to those of skill in the art. As described below, conjugation can be effected by chemical means, through covalent, ionic or any other suitable linkage. For example, the reagents and methods for conjugation as disclosed in WO 01/02600 can be used.

In some embodiments, the conjugate is a fusion protein, which can be isolated or purified through affinity binding between the protein or peptide fragment of the fusion protein and an affinity binding moiety. Any kind of affinity interaction can be used for isolating or purifying the fusion protein. The affinity interactions, such as those described herein, but not limited to, are protein/protein, protein/nucleotide, protein/lipid, protein/polysaccharide, or protein/metal interactions.

In other embodiments, the conjugate can be attached to a surface. More preferably, the conjugate can be attached to the surface through affinity binding between the facilitating agent of conjugate and an affinity binding moiety on the surface. Any kind of affinity interaction can be used for attaching the conjugate, including the protein/protein, protein/nucleotide, protein/lipid, protein/polysaccharide, or protein/metal interactions.

In yet another aspect, the present invention is directed to a pharmaceutical composition, which pharmaceutical composition comprises an isolated nucleic acid fragment which isolated nucleic acid fragment hybridizes, under low, middle or high stringency, with a sequence of nucleotides, or a complementary strand thereof, encoding an extracellular domain of the ErbB-3 protein, or a functional fragment thereof, comprising an amino acid sequence set forth in SEQ ID NO:2 or SEQ ID NO:3 or at least amino acid residues 24-81 of the amino acid sequence set forth in SEQ ID NO: 14 or at least amino acid residues 2-139 of the amino acid sequence set forth in SEQ ID NO:16 and a pharmaceutically acceptable carrier or excipient. Preferably, the isolated nucleic acid comprises a sequence of nucleotides, or a complementary strand thereof, encoding an extracellular domain of the ErbB-3 protein, or a functional fragment thereof, comprising an amino acid sequence set forth in SEQ ID NO:2 or SEQ ID NO:3 or at least amino acid residues 24-81 of the amino acid sequence set forth in SEQ ID NO:14 or at least amino acid residues 2-139 of the amino acid sequence set forth in SEQ ID NO: 16. The pharmaceutical composition can further comprise an immune response potentiator and/or an anti-neoplasm agent. Vaccines, comprising the above isolated nucleic acid fragments, alone or in combination with an immune response potentiator, are also provided. Combinations, comprising the above isolated nucleic acid fragments with an anti-neoplasm agent, and optionally a pharmaceutically acceptable carrier or excipient, are also provided.

In yet another aspect, the present invention is directed to a pharmaceutical composition, which pharmaceutical composition comprises a substantially purified protein or peptide, which comprises an extracellular domain of the ErbB-3 protein, or a functional fragment thereof, comprising an amino acid sequence set forth in SEQ ID NO:2 or SEQ ill NO:3 or at least amino acid residues 24-81 of the amino acid sequence set forth in SEQ ID NO:14 or at least amino acid residues 2-139 of the amino acid sequence set forth in SEQ ID NO: 16 and a pharmaceutically acceptable carrier or excipient. The pharmaceutical composition can further comprise an immune response potentiator and/or an anti-neoplasm agent. Vaccines, comprising the above substantially purified proteins or peptides, alone or in combination with an immune response potentiator, are also provided. Combinations, comprising the above substantially purified proteins or peptides with an anti-neoplasm agent, and optionally a pharmaceutically acceptable carrier or excipient, are also provided.

In yet another aspect, the present invention is directed to an antibody, which antibody binds to an epitope in an extracellular domain of the ErbB-3 protein, or a functional fragment thereof, comprising an amino acid sequence set forth in SEQ ID NO:2 or SEQ ID NO:3 or at least amino acid residues 24-81 of the amino acid sequence set forth in SEQ ID NO:14 or at least amino acid residues 2-139 of the amino acid sequence set forth in SEQ ID NO:16. Preferably, the antibody binds specifically to an epitope in an extracellular domain of the ErbB-3 protein, or a functional fragment thereof, comprising an amino acid sequence set forth in SEQ ID NO:2 or SEQ ID NO:3 or at least amino acid residues 24-81 of the amino acid sequence set forth in SEQ ID NO:14 or at least amino acid residues 2-139 of the amino acid sequence set forth in SEQ ID NO:16.

The antibody can be in any suitable form. For example, the antibody can a polyclonal, monoclonal, chimeric, single chain, human or humanized antibody (See e.g., U.S. Pat. No. 5,968,511). The antibody, in various forms, can be made according to any methods known in the art (See, e.g., Coligan et al. (Ed.), Current Protocols in Immunology, John Wiley & Sons, Inc. (2000)). Pharmaceutical compositions, comprising the above antibodies, alone or in combination with anti-neoplasm agent, and a pharmaceutically acceptable carrier or excipient are also provided.

D. EXAMPLES

The following are exemplary embodiments provided for illustrative purposes only.

The inventor discovered the effect and method of B3, DE3-1, rhErbB3-f12 and rhErbB3-f78 as an anti-tumor vaccine in the treatment of human cancer such as breast cancer.

The inventor discovered that B3, DE3-1, rhErbB3-f12 and rhErbB3-f78 as an anti-tumor vaccine can significantly lower the incidence of the development of human cancer such as breast cancer in high-risk population.

The inventor provided a method of B3, DE3-1, rhErbB3-f12 and rhErbB3-f78 as an anti-tumor vaccine significantly lowering the incidence of the development of human cancer such as breast cancer in high-risk population The inventor discovered that there was significant effect of B3, DE3-1, DE3-1, rhErbB3-f12 and rhErbB3-f78 as an anti-tumor vaccine on postponing the tumor development such as human breast cancer.

The inventor discovered that there was significant inhibitory effect of B3, DE3-1, rhErbB3-f12 and rhErbB3-f78 as an anti-tumor vaccine on the tumor development such as human breast cancer.

The inventor discovered a method of inhibiting cancerous growth such as breast cancer and that was achieved through inducing immune responses.

The aforementioned cells may be a tumor cells, much probably they are human breast cancer cells and other cancerous cells with Erb2/ErbB3 over-expression.

It is ErbB3 protein antigen expressed through genetic engineering that made the aforementioned method come true; De3-1, rhErbB3-f12 and rhErbB3-f78 is a protein expressed by E. Coli; B3 was an antigen of protein expressed by Eucaryotic cells or ErbB3 antigen produced by other methods, ErbB3 antigen may be ErbB3 molecule or part of a segment of the molecule.

Under a typical condition of cancer treatment such as breast cancer, ErbB3 vaccine, which is produced by different methods can inhibit tumor growth under certain dosage level.

The aforementioned cancers included breast cancer, ovary carcinoma, gastric carcinoma, and prostate carcinoma and lung cancer.

The following description will make the aforementioned invention more clear.

1. Experimental Material and Methods

Preparation of B3,De3-1, rhErbB3-f12 and rhErbB3-f78

The vaccine involved in the present experiment included protein molecule in the extra-cell membranes region of ErbB3 and part of the protein segment of the extra-cell membranes, they are named as B2 and SD32. The protein molecule in the extra-cell membranes region of ErbB3 and part of the protein of the extra-cell membranes serves as an experiment sample, they are named as B3, De3-1, rhErbB3-f12 and rhErbB3-f78 here; the aforementioned vaccines are manufactured by Zensun (Shanghai) Science and Technology Development Co Ltd. The preparation of B3 and DE3-1, rhErbB3-f12 and rhErbB3-f78 is as follow:

Preparing B3

B3 gene is the encoded cDNA sequence of protein of ErbB3 extra-cell membrane region (FIG. 1); amplified with PCR, sequence of the primer was:

```
Primer1,
                                                 (SEQ ID NO:6)
5'TCTGCGGAGTCATGAGGGC Primer2,
                                                 (SEQ ID NO:7)
3'TCACTTGTCGTCATCGTCCTTGTAGTCTTTGCCGATCAGCACCAGTGT
```

The italics are flag sequence.

After PCR amplification, the targeting gene was cloned into pMD-18T vector; the transformer will be cut by BamHI/SalI after enzyme digestion and identified of the sequence to be correct, then connected to pCDNA3BamHI/xhoI.

Figure 4:
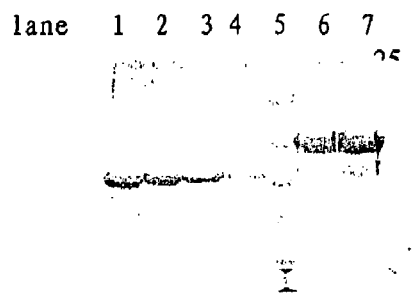
FIG. 4 illustrates isolation and/or purification and SDS-PAGE analysis of B3 protein. Lane1-4: BSA control, 10 ug, 5 ug, 3 ug, 1 ug/lane respectively. Lane5: Protein marker, 7708S NEB. Lane6-7: B3 protein expressed for COS7.

Establishment and screening of high performance engineering bacteria: After identification through PCR and enzyme digestion, the engineering bacteria went through 15% SDS-PAGE electrophoresis, thin layer scanning analysis, affinity chromatography, Western-blotting identification and repeated screening a stable high expressive targeting protein engineering bacteria. FIG. 4 illustrated the B3 protein purification, affinity chromatography purification. FIG. 5 showed the targeting protein and amino acid sequence of B3 purified protein after amino acid sequencing.

DE3-1 Preparation

Figure 7:
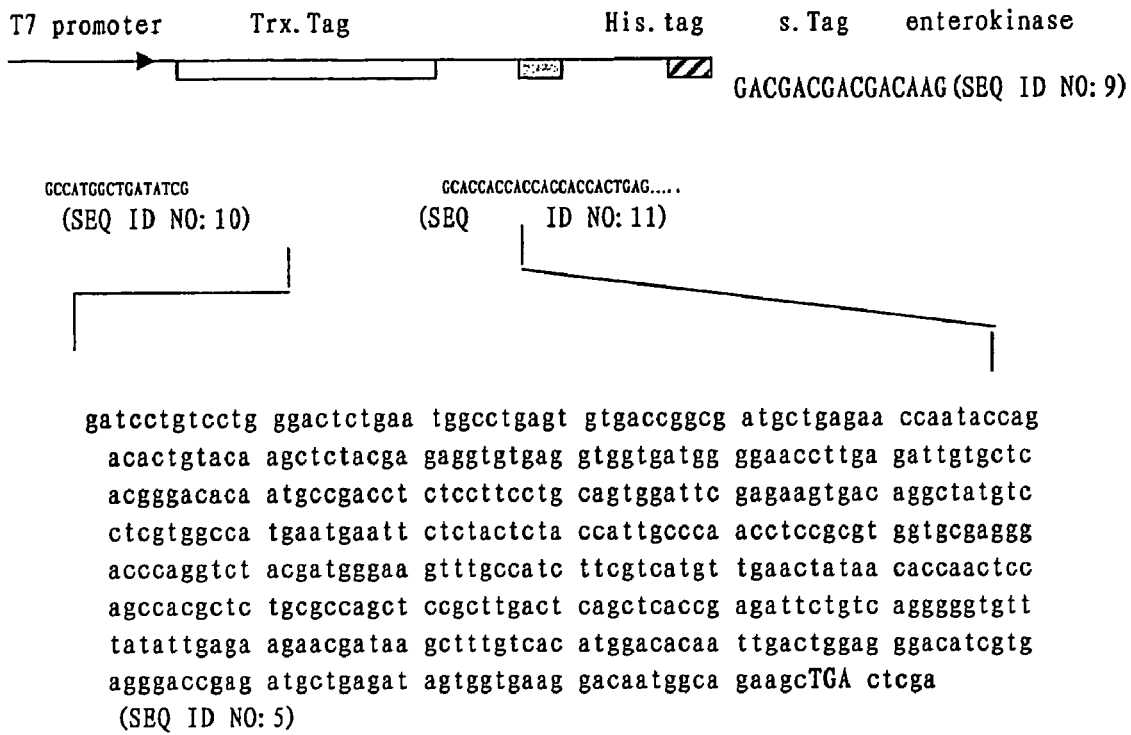
FIG. 7 illustrates DE3-1 plasmid construction.
Figure 8:
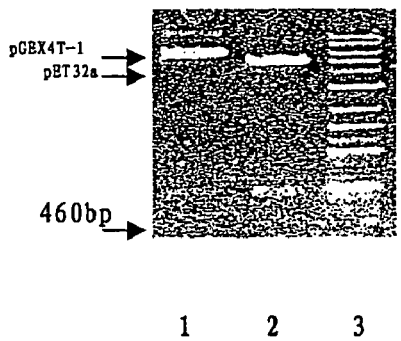
FIG. 8 illustrates restriction enzyme digestion of DE3-1 plasmid. Lane 1: DE3-1 in pGEX4T-1, cut with BamHI/XhoI. Lane2: DE3-1 in pET32a, cut with BamHI/XhoI. Lane3: 1 Kd ladder (NEB).

FIG. 6 showed cDNA sequence of encoded extra-cell membrane ErbB3 protein segment of PCR amplified targeting gene. Structure of the expressed plasmid: targeting gene segment was cut out with BamHI/XhoI from pGEX4T-1 vector (Phamacia company), connecting into pET32a vector (Novagen company) BabHI/XhoI, the protein was expressed by T7 promotor, N end fused with Trx Tag, His Tag and S-Tag, FIG. 7 illustrates the diagram. FIG. 8 illustrates the identification of the plasmid composition.

Figure 9:
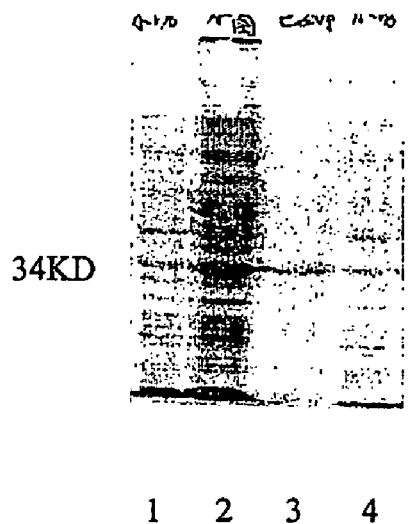
FIG. 9 illustrates SDS-PAGE analysis of DE3-1 expression. Lane1: before induction. Lane2: after induction. Lane3: inclusion body. Lane4: supernatant after sonication.
Figure 10:
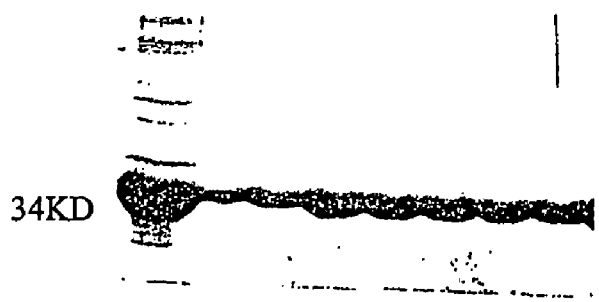
FIG. 10 illustrates isolation and/or purification and SDS-PAGE analysis of DE3-1 protein. Lane1: Flow through. Lane2-8: Eluates from NTA His tag affinity column.

DE3-1 protein expression: Transferring the plasmid into BL21 strain, inoculated the strain into 5 ml of LB+AP, over night; 1:100 inoculated into pre-warmed LB+AP, 37° C. for 2.5-3 hours (OD=0.6); induction with IPTG at 37° C. for 3 hours or 30° C. for 8 hours; centrifuge at 4° C., 6K for 10 minutes, take out the supernatant, put the sediment on ice; PBS suspension was made with cold, 1/20 bacteria solution, then crashed by ultrasound; centrifuge at 4° C. , 12K for 10 minutes, large amount of 34 KD targeting gene is harvested (FIG. 9). Purified the DE3-1 protein; DE3-1 emerges in the inclusion bodies, dissolved with 6M guanidine hydrochloride, dialyzed in NTA-O buffer solution (Histag purified solution), good duplicated condition, purified with Histag affinity chromatography (bought from Bo-Cai Company) FIG. 10, after amino acid sequencing, the purified DE3-1 protein was in consistent with the targeting protein sequence, FIG. 11 showed the amino acid sequence.

rhErbB3-f12 and rhErbB3-f78 (SEQ ID NO:16) Preparation rhErbB3-f12 (SEQ ID NO:14) gene is the encoded cDNA sequence of protein of ErbB3 extra-cell membrane region; amplified with PCR, sequence of the primer was:

```
P1:
                                                 (SEQ ID NO:12)
5'-TGG CCA TGG ACA TCA AGC ATA ATC GGC C-3'
(1645-1664)
       NcoI
P2:
                                                 (SEQ ID NO:13)
3'-GTG CTC GAG AGG CTC CCC ATT CAG AAA G-5'
(1800-1818)
       XhoI
```

Experiment on the A-tumor Effect of B3, DE3-1

The preventive effect of B3, DE3-1 on tumor development.

8-10 weeks old FVB/N transgenic mice (bought from Jackson Lab USA) was selected as experiment animals, the mice were divided into 5 groups with 40 mice each, they were control group, B2, B3 and DE3-1 group; BSA, B2, SD32, B3, DE3-1 was mixed with Freud's adjuvant (CFA, complete Freud's adjuvant, bought from Sigma company) and injected abdominally every 20 days for 7 injections respectively to various groups. The dosage of BSA, B2, SD32, B3 and DE3-1 vaccine was 10, 5, 10, 1 and 10 μg/mouse/injection. Weekly monitor tumour development. The tumour development was verified and analysed statistically.

Therapeutic Effect of B3, DE3-1, Against Tumour

Transplanted tumour model, after immunohistological screening test, about 1000 $mm^3$ tumour mass was cut down from spontaneous tumour of neu protein over-expressed FVB/N transgenic mice. The tumour mass was abraded into single cells with nylon net, the amount injected under the breast of each FVB/N trans-genic mice was $5 \times 10^6$ cells. About 10-14 days after inoculation, tumor was palpable (>5 mm) in the control group, demonstrating that the animal model was established successfully.

Nothing was administered in the control group; 24 hours after the inoculation, SD32 and B3 vaccine injection started in SD32 and B3 experiment groups, the aforementioned vaccines were absorbed on 0.1 mg/ml of Al(OH)3 respectively, and injected multi-pointedly every 2 weeks for a total of three injections; the experiment was completed in 14 days after the third injection. Morbidity was monitored weekly, tumor size was measured weekly with vernier. Volume (length diameter×short diameter 2/2) of the tumor was used to represent their size, and curve of tumor growth was protracted, Tumor weight was measured after completion of the experiment and tumor-inhibitory rate was calculated, inhibitory rate=[(tumor weight of control group−tumor weight of experiment groups)/tumor weight of control group]×100.

Experiment on the Therapeutic Effect of Various Dosage of DE3-1 rhErbB3-f12 and rhErbB3-f78 on Immune Therapy Against Tumor Preparing animal and transplanted animal tumor model: The same as (Experiment on therapeutic effect of B3 and DE3-1 rhErbB3-f12 and rhErbB3-f78 vaccine on immune therapy against tumor). No treatment was given to the control group, histag protein was injected to the negative control group, and Adriamycin (Santou MingZhi Pharmaceuticals) was administered for the positive control group, 5 μg, 20 μg and 80 μg was given to DE3-1 group respectively.

One day after the inoculation, Adriamycin 2.2 mg/kg was injected abdominally for consecutive 7 days in mice of the positive control group; histag protein+Al(OH)3 was injected abdominally for mice of the negative control group; In DE3-1 group, the vaccine was absorbed on 0.1 mg of Al(OH)3 and multi-points subcutaneous injection every 2 weeks for a total of 3 injections were carried out in mice. The experiment completed in 14 days after the third injection. Tumor development was monitored weekly, tumor size was measured with vernier and the size was expressed as (length diameter× short diameter 2/2), curve of tumor growth was protracted and analyzed statistically.

Tumor weight was measured after completion of the experiment and tumor-inhibitory rate was calculated, tumor inhibitory rate=[(tumor weight of control group−tumor weight of experiment groups)/tumor weight of control group]×100.

Experiment on Cross Immunity of B2 and B3 Antigen

FVB transgenic mice were immuned with B2 protein and B3 protein respectively, 10 days thereafter, blood was withdrawn and antibody titer was tested with ELISA. 0.3 ug/hole of B2 and B3 was wrapped, 1:1000 B2 and B3 on each plate were titrated with standard serum respectively, cultured at 37° C. for 30 minutes, sealed with 1% BSA, added double antibody, color development for 15 minutes with DAD, tested with Bio-Rad 450 nm enzyme labeled device.

2. Experiment Results and Discussion

Figure 12:
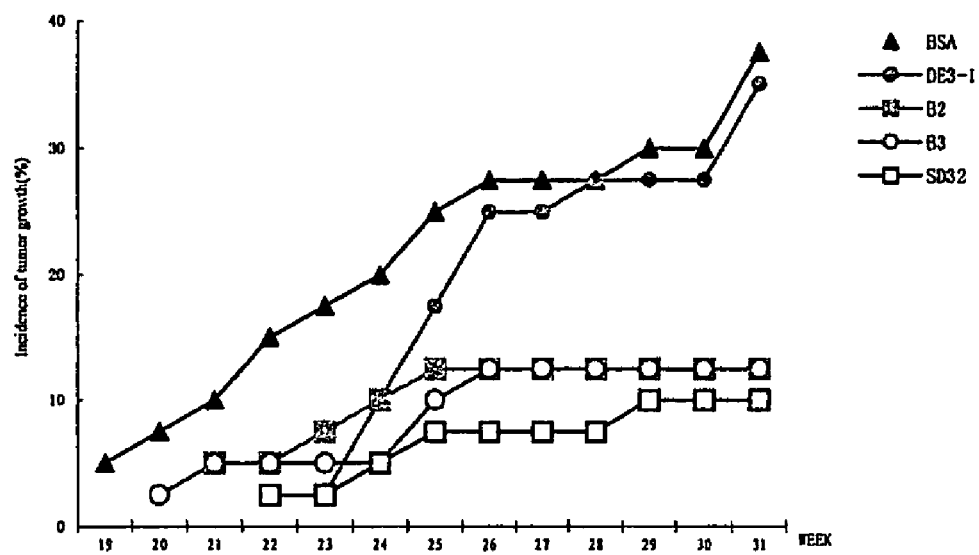
FIG. 12 illustrates the effect of various vaccines on incidence of FVB/N transgenic mice

Table 1 and FIG. 12 illustrate the experimental results of tumor inhibitory effect of B3 and DE3-1.

TABLE 1

Experimental results of tumor inhibitory effect of B3 and DE3-1 vaccine

| Grouping | Case number | Treatment | Dosage (μg/animal/dose) | Time of tumor occurrence (weeks) | Incidence of tumor growth (%) |
|---|---|---|---|---|---|
| Negative control group | 40 | BSA + CFA | 10 | 19 | 37.5 |
| B2 experiment group | 40 | B2 + CFA | 5 | 21 | 12.5 |
| SD32 experiment group | 40 | SD32 + CFA | 10 | 22 | 10 |
| B3 experiment group | 40 | B3 + CFA | 5 | 20 | 12.5 |
| DE3-1 experiment group | 40 | DE3-1 + CFA | 10 | 23 | 35 |

Objective of the present experiment is to explore whether there is preventive effect of B3 or DE3-1 vaccine on tumor development. The reason to choose this type of transgenic mice as experiment animal model, is because rat wild type neu cDNA controlled by mice breast virus promotor was transferred into the body of mice and produce over-expression of neu protein and spontaneous breast cancer occurred within 5-8 months in half of the mice. Natural course of tumor in the transgenic mice and its pathologic pattern is similar to that of human breast cancer. Therefore, it may have better therapeutic effect when used clinically. The sample contains 40 animals in each group, the aim of selecting such large sample is to ensure the number of cases which have the disorders will be greater than 10 animals, thus will be of greater implication statistically. The selection of dosage is based on the results of pre-experiments.

Transgenic mice were immunized with BSA, B2, B3, SD32 and DE3-1 respectively, as we can see from the tables and figures, the tumor incidence of 37.5% began from the 19th week on in the negative control group; whereas the time of tumor development in SD32, B3 and B2 group was 21, 22, and 20 weeks with their incidence of 10%, 12.5% and 12.5% respectively, demonstrating that there were significant tumor-inhibitory effect of SD32, B3 and B2 vaccine against the development of tumor (P<0.025; ×2 testing); at the same time, they can postpone the time of tumor development. The occurrence of tumor in DE3-1 group is later than that in the control group, however the tumor incidence of 35% was not significantly different from that of the control group (P<0.05; ×2 testing).

Experimental Results of Anti-tumor Effect of B3 and DE3-1 Vaccine

Figure 13:
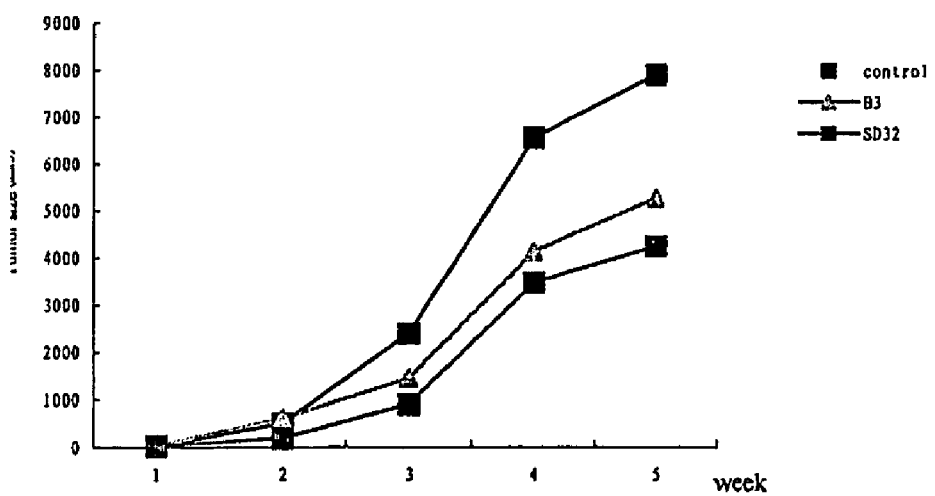
FIG. 13 illustrates the effect of various drugs on tumor growth in mice (5 weeks).
Figure 14:
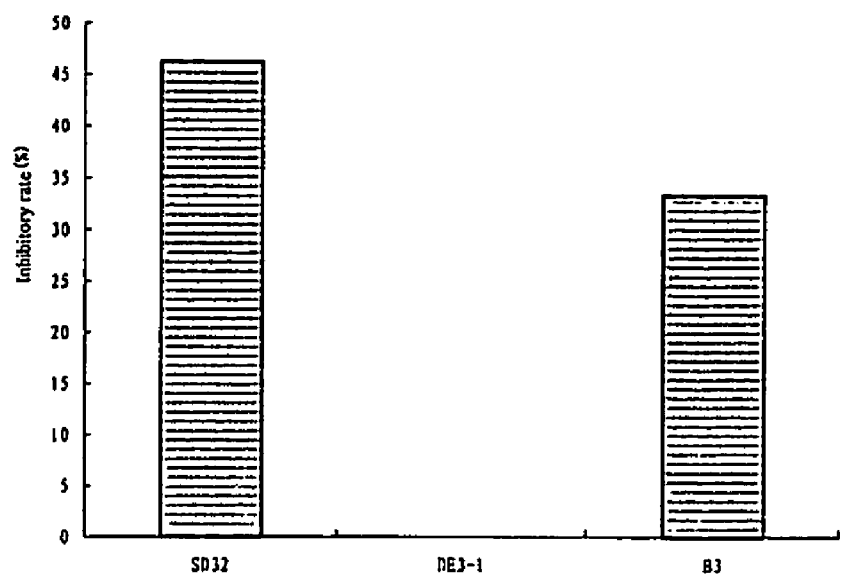
FIG. 14 illustrates the tumor-inhibitory effect of various drugs against tumor growth (5 weeks).

Table 2 and FIG. 13-14 show experimental results of anti-tumor effect of B3 vaccine

TABLE 2

Experimental results of anti-tumor effect of B3 and DE3-1

| Grouping | Treatment | Tumor size (mm3) | Tumor weight (g) | Inhibitory rate (%) |
|---|---|---|---|---|
| Negative control group | histag protein + Al(OH)3 | 7849.8 ± 849.8 | 5.76 ± 0.55 | |

TABLE 2-continued

Experimental results of anti-tumor effect of B3 and DE3-1

| Grouping | Treatment | Tumor size (mm3) | Tumor weight (g) | Inhibitory rate (%) |
|---|---|---|---|---|
| SD32 experiment group | SD32 + Al(OH)3 | 4246.5 ± 540.6 | 3.28 ± 0.36 | 46 |
| B3 experiment group | B3 + Al(OH)3 | 5271.8 ± 658.9 | 3.13 ± 0.33 | 33 |

In order to identify the anti-tumor therapeutic effect of B3, the inventor carried out experiment on immune therapy with B3 in transplanted tumor model.

Table 2 and FIG. 13-14 illustrate the effect of various vaccines on tumor growth in mice, demonstrating that the tumor-inhibitory rate of SD32 and B3 were 46% and 33% respectively, and that both of them had significant tumor-inhibitory effect (P<0.01; t testing).

Experimental Results of Anti-tumor Effect of DE3-1, rhErbB3-f12 and rhErbB3-f78

Figure 15:
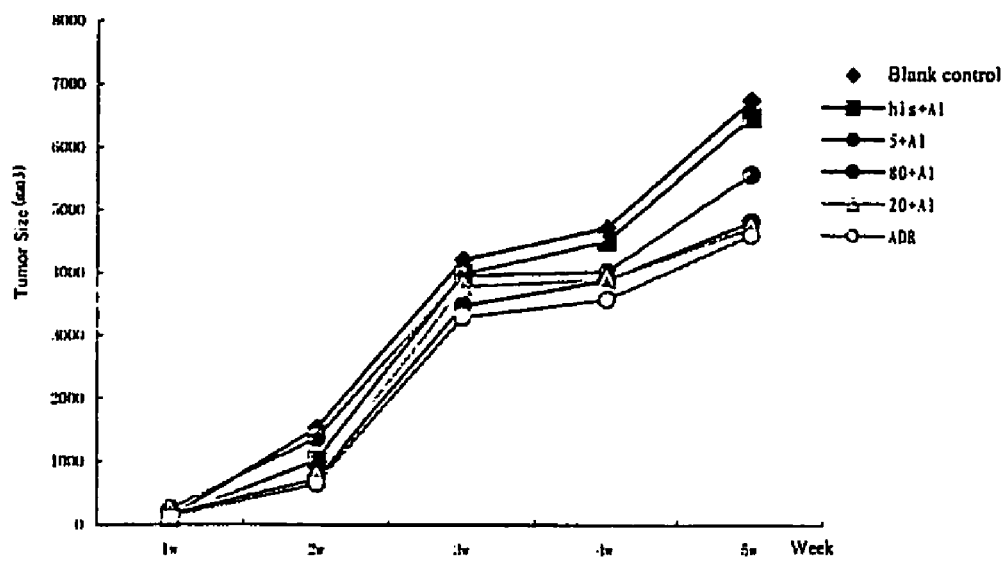
FIG. 15 illustrates the effect of DE3-1 on the growth of breast cancer in mice (5 weeks).
Figure 16:
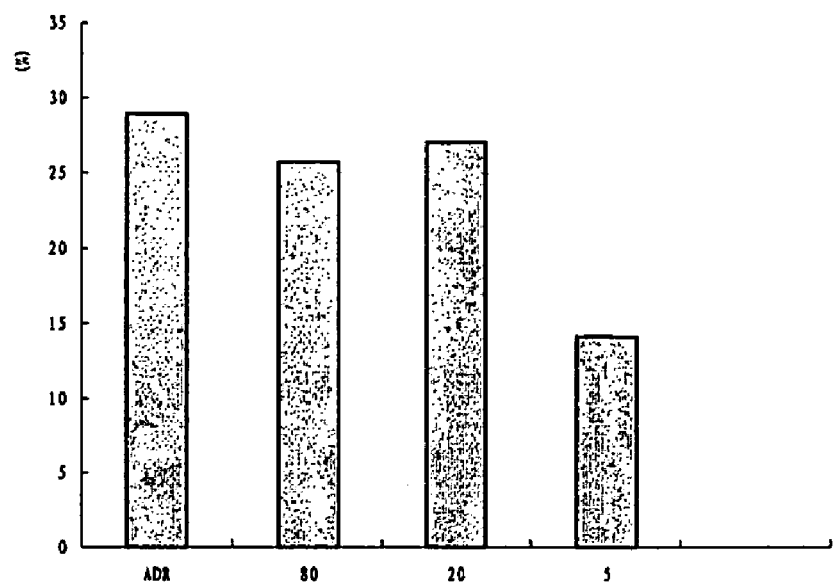
FIG. 16 illustrates the tumor-inhibitory rate of DE3-1 against tumor growth (5 weeks).

Dosage of 5 μg, 20 μg and 80 μg/animal were used to immunized mice in the experiment group, table 3 and FIG. 15-16 showed the experimental results.

TABLE 3

Experimental results of anti-tumor effect of DE3-1

| Grouping | Case number | Treatment | Tumor size (mm3) | Tumor weight (g) | Inhibitory rate % |
|---|---|---|---|---|---|
| Control group | 8 | | 6742.9 ± 657.8 | 4.769 ± 0.56 | |
| Negative control group | 8 | histag protein + Al(OH)3 | 6476.9 ± 567.9 | 4.461 ± 0.52 | |
| Positive control group | 8 | ADR 2.2 mg/kg | 4603.1 ± 478.3 | 3.564 ± 0.42 | 25.3 |
| DE3-1 experiment group | 8 | 80 μg DE3-1 + Al(OH)3 | 4810.8 ± 460.5 | 3.658 ± 0.37 | 26.3 |
| DE3-1 experiment group | 8 | 20 μg DE3-1 + Al(OH)3 | 4715.0 ± 434.8 | 3.455 ± 0.41 | 28.9 |
| DE3-1 experiment group | 8 | 5 μg DE3-1 + Al(OH)3 | 5563.7 ± 600.6 | 3.687 ± 0.45 | 22.4 |

Tumor-inhibitory rate and measured tumor size was consistent among groups with various dosage of DE3-1, the best tumor-inhibitory effect was seen in 20 μg level of DE3-1, reaching about 28.9%. After completion of the experiment, the mice were killed, took out the tumor and measured their weight; there were significant difference (P<0.001, t test) between the positive control group, groups with various dosage level, negative control group and placebo control group. The tumor-inhibitory rate of 5 μg, 20 μg and 80 μg dosage level group were 26.3%, 22.4% and 28.9% respectively.

TABLE 4

Experimental results of anti-tumor effect of rhErbB3-f12

| Grouping | Case number | Dosage (mg/kg) | Treatment | Tumor weight (g) | Inhibitory rate % |
|---|---|---|---|---|---|
| Negative control | 14 | | sc × 3q14d | 5.55 ± 1.25 | |
| Positive control (Taxol) | 7 | 10 | ip × 7qd | 3.09 ± 1.08* | 44.32 |
| rhErbB3-f12 | 7 | 1 | sc × 3q14d | 2.40 ± 0.49* | 56.76 |
| rhErbB3-f12 | 7 | 0.5 | sc × 3q14d | 2.62 ± 0.67* | 52.61 |
| rhErbB3-f12 | 7 | 0.25 | sc × 3q14d | 2.31 ± 0.40* | 58.39 |

TABLE 5

Experimental results of anti-tumor effect of rhErbB3-f78

| Grouping | Case number | Dosage (mg/kg) | Treatment | Tumor weight (g) | Inhibitory rate % |
|---|---|---|---|---|---|
| Negative control | 14 | 2.5 | sc × 3q14d | 1.098 ± 0.17 | |
| Positive control (ADM) | 7 | 2 | ip × 7qd | 0.648 ± 0.27* | 40.98 |
| rhErbB3-f78 | 7 | 2.5 | sc × 3q14d | 0.435 ± 0.12* | 60.38 |

Experiment on Cross Immunity Between B2 and B3 Antigen

Figure 17:
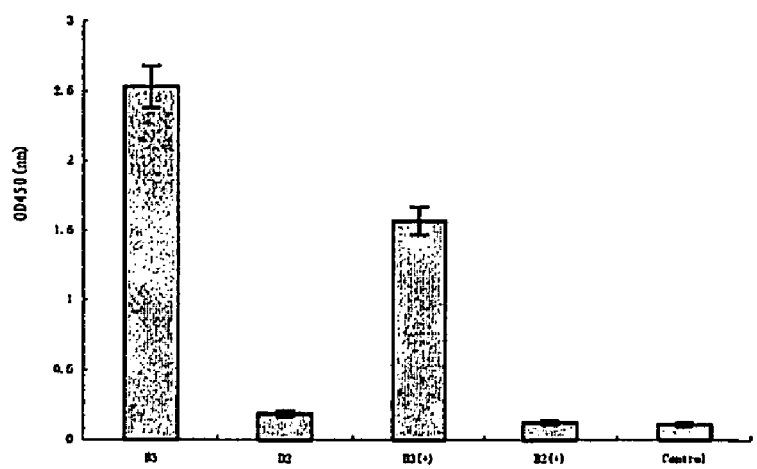
FIG. 17 illustrates experiment on cross immunity between B2 and B3 antigen (B3 protein wrapped).
Figure 18:
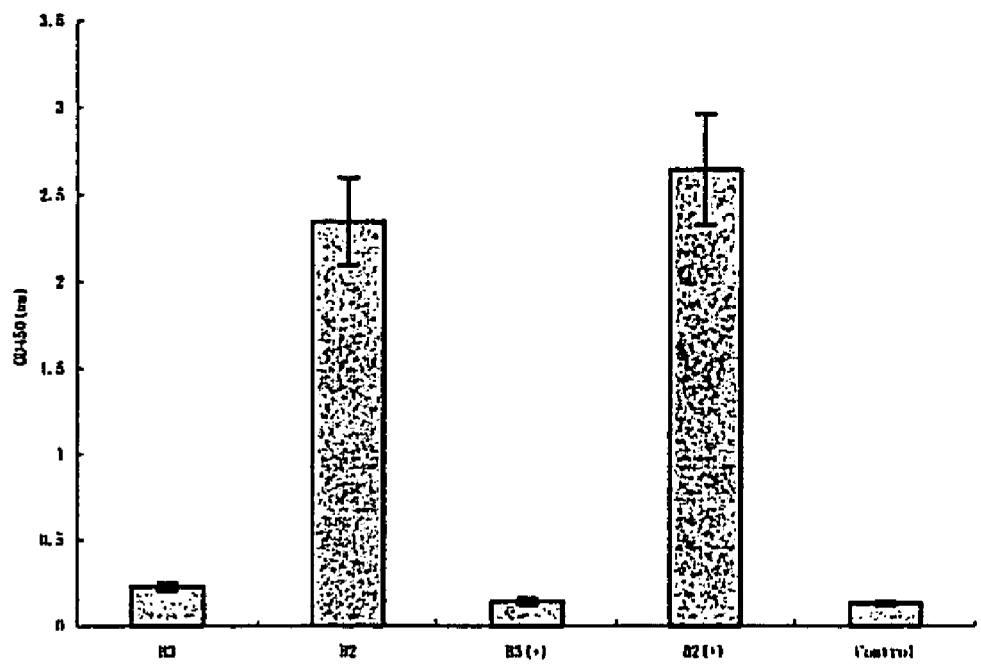
FIG. 18 illustrates experiment on cross immunity between B2 and B3 antigen (B2 protein wrapped).
Figure 19:
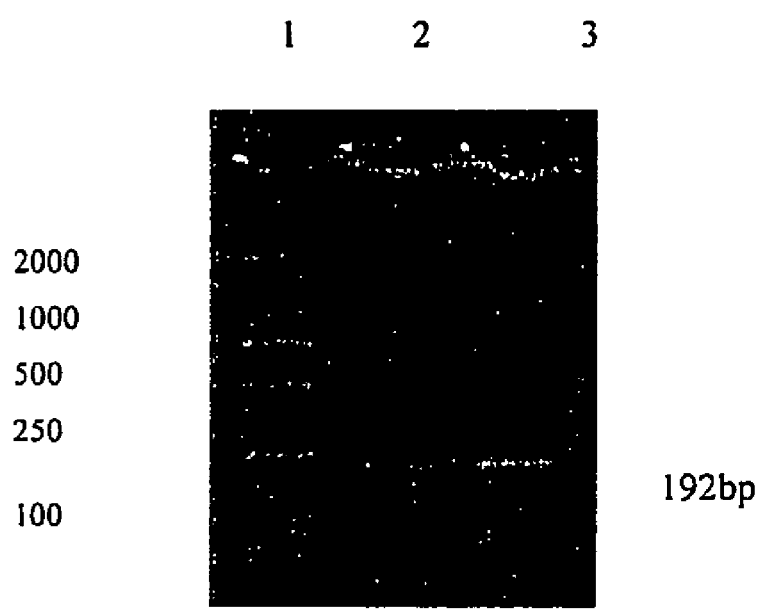
FIG. 19 illustrates Result of PCR amplification Lane 2,3: 192 bp ErbB3-f12 gene obtained by RT-PCR; Lane 1: DNA marker
Figure 20:
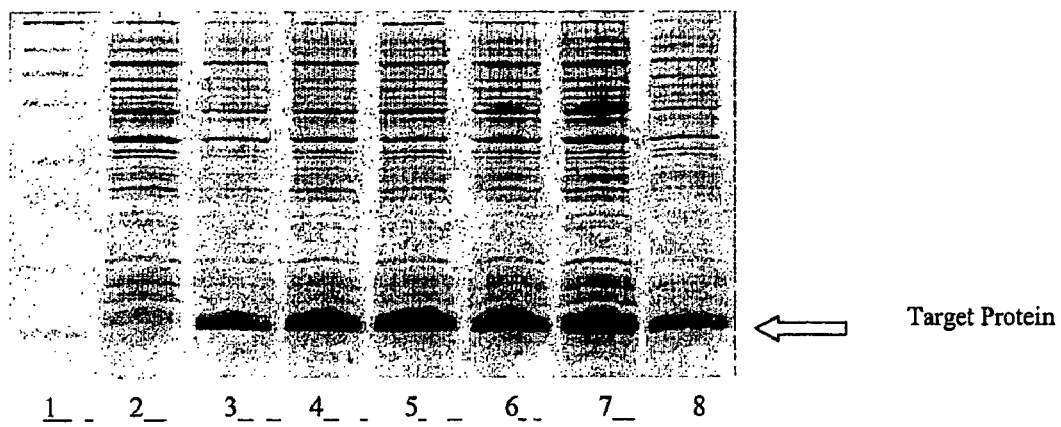
FIG. 20 illustrates Screening for expression engineering strain.
Figure 21:
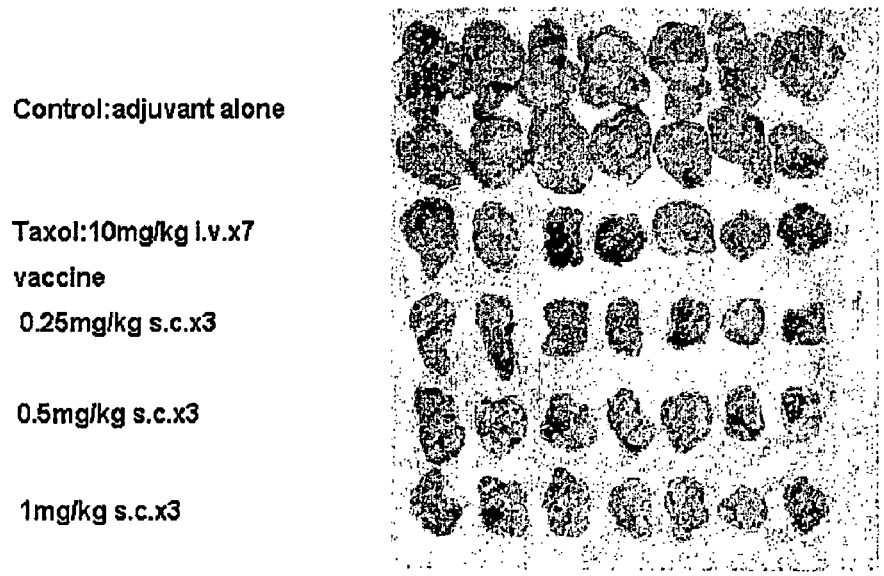
FIG. 21 illustrates Experimental results of anti-tumor effect of rhErbB3-f12.

The objective of experiment on cross immunity between B2 and B3 antigen is to explore whether there exists cross immunity between B2 and B3 antigen. FIG. 17-18 showed the experimental results demonstrating that there isn't any cross immunity between B2 and B3 antigen.

3. Summary

In this research, we discovered new promising vaccines of B3 and DE3-1, which are designed on the basis of a new anti-tumor targeting ErbB3, and have preventive effect on tumor development and immune therapeutical effect against tumor.

The over-expression of ErbB2 receptor existed in part of adenocarcinoma discovered in the previous studies was considered to be associated with cancer development after formation of homogenous dimer. Over-expression of ErbB2 was considered to be the major cause of adenocarcinoma development, it is due to: 1) the amplification of ErbB2 gene existed in tumor cells such as breast cancer and ovary carcinoma was the cause of over-expression of ErbB2; 2) Overexpression of ErbB2 leads to phosphorylation in its cellular functional area and affects the interaction between intracellular signal molecule Shc and ErbB2; 3) the transfection of wild type ErbB2 into fibroblast can lead to cell transformation; 4) the enhancement of the formation of ErbB2 variants from ErbB2 homogenous dimer can also enhance its activity of cell transformation.

Prior to the present discovery, the inventors have discovered ErbB3 as another new anti-tumor target in addition to ErbB2. The inventors clarify that over-experssion of ErbB2 receptor leads to the formation of heterogenous dimer from ErbB2 and ErbB3, and that was the cause of cancer development. Discovery of this new target provides us with new concept of anti-cancer therapeutical method: use extra-cell membrane protein of ErbB3 cells for cancer prevention and treatment, to lower the incidence of breast cancer and produce effect against tumor growth.

The tremendous success of humanized monoclonal antibody-herceptin targeted on ErbB2 is based on the relativity between over-expression of ErbB2 and occurrence of various tumors. However, the co-expression of ErbB2 and ErbB4 receptors in myocardial cells leads to the formation of heterogenous dimer from ErbB2 receptor and ErbB4 receptor; the dimer was very important in the maintain of normal structure of myocardial cells, thus, anti-cancer medicine targeting on ErbB2 receptor has damages on myocardial cells and leads to heart failure; however, anti-cancer drug targeting at ErbB3 receptor doesn't have this adverse reaction. Therefore, the use of ErbB3 as a specific anti-tumor vaccine against breast cancer, ovary carcinoma, gastrocarcinoma, prostate cancer, rectal cancer and lung cancer will play a very important role in the prevention and treatment of these cancers.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A method for treating a neoplasm which expresses ErbB-3 in a mammal, which method comprises administering to a mammal, to which such treatment is needed or desirable, an effective amount of an ErbB-3 protein or a nucleic acid that encodes and expresses said ErbB-3 protein, whereby an immune response is generated against said neoplasm, wherein the ErbB-3 protein is a fragment of the extracellular domain of ErbB3 and comprises:
   (a) the amino acid sequence set forth in SEQ ID NO:3; or
   (b) amino acid residues 24-81 of the amino acid sequence set forth in SEQ ID NO:14; or
   (c) amino acid residues 2-139 of the amino acid sequence set forth in SEQ ID NO:16,
   wherein the ErbB-3 protein is not the entire extracellular domain of ErbB3.

2. The method of claim 1, further comprising administering an immune response potentiator to the mammal.

3. The method of claim 1, wherein the ErbB-3 protein or the nucleic acid that encodes and expresses said ErbB-3 protein is co-administered with a pharmaceutically acceptable carrier or excipient.

4. The method of claim 1, wherein the ErbB-3 protein or the nucleic acid that encodes and expresses said ErbB-3 protein is co-administered with an anti-neoplasm agent.

5. The method of claim 4, wherein the anti-neoplasm agent is selected from the group consisting of an anti-angiogenic agent, an alkylating agent, an antimetabolite, a natural product, a platinum coordination complex, an anthracenedione, a substituted urea, a methylhydrazine derivative, an adrenocortical suppressant, a hormone, an antagonist, an oncogene inhibitor, a tumor suppressor gene or protein, an anti-oncogene antibody and an anti-oncogene antisense oligonucleotide.

6. The method of claim 1, wherein the neoplasm to be treated is selected from the group consisting of adrenal gland, anus, auditory nerve, bile ducts, bladder, bone, brain, breast, bruccal, central nervous system, cervix, colon, ear, endometrium, esophagus, eye, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve and vulva neoplasm.

7. The method of claim 1, wherein the neoplasm to be treated is selected from the group consisting of breast, ovary, stomach, prostate, colon and lung cancer.

8. The method of claim 1, wherein the neoplasm to be treated is breast cancer.

9. The method of claim 1, wherein the mammal is a human.

10. The method of claim 9, wherein the administering is by subcutaneous injection.

11. The method of claim 1, wherein the administering is by intracavernous injection, subcutaneous injection, intravenous injection, intramuscular injection, intradermal injection, oral administration or topical administration.

12. The method of claim 1, wherein the ErbB-3 protein is administered to the neoplasm in situ.

13. The method of claim 12, further comprising administering an immune response potentiator to the neoplasm in situ.

* * * * *